US009474789B2

(12) United States Patent
Ricardo et al.

(10) Patent No.: US 9,474,789 B2
(45) Date of Patent: *Oct. 25, 2016

(54) METHODS AND COMPOSITIONS FOR PROMOTING ORGAN GROWTH AND DEVELOPMENT

(71) Applicant: Kintan Pty Ltd., Howlong, NSW (AU)

(72) Inventors: Sharon Denise Ricardo, Mornington (AU); David Arthur Hume, Scotland (GB); Melissa Helen Little, Brisbane (AU); Christina Victoria Jones, Wheelers Hill (AU)

(73) Assignee: KINTAN PTY LTD., Howlong, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/524,825

(22) Filed: Oct. 27, 2014

(65) Prior Publication Data

US 2015/0164992 A1 Jun. 18, 2015

Related U.S. Application Data

(63) Continuation of application No. 13/685,327, filed on Nov. 26, 2012, now abandoned, which is a continuation of application No. 13/236,177, filed on Sep. 19, 2011, now Pat. No. 8,338,370, which is a continuation of application No. 11/902,062, filed on Sep. 18, 2007, now abandoned, which is a continuation-in-part of application No. PCT/AU2007/001372, filed on Sep. 17, 2007, and a continuation-in-part of application No. PCT/AU2006/000357, filed on Mar. 17, 2006.

(30) Foreign Application Priority Data

| Mar. 18, 2005 | (AU) | ................................. 2005901346 |
| Sep. 15, 2006 | (AU) | ................................. 2006905099 |
| Sep. 18, 2006 | (AU) | ................................. 2006905156 |

(51) Int. Cl.
| A61K 38/00 | (2006.01) |
| A61K 38/19 | (2006.01) |
| A61K 31/70 | (2006.01) |
| A61K 31/7088 | (2006.01) |
| A61K 35/12 | (2015.01) |
| A61K 38/18 | (2006.01) |

(52) U.S. Cl.
CPC ............. *A61K 38/193* (2013.01); *A61K 31/70* (2013.01); *A61K 31/7088* (2013.01); *A61K 35/12* (2013.01); *A61K 38/18* (2013.01)

(58) Field of Classification Search
CPC .................................................. A61K 38/193
See application file for complete search history.

(56) References Cited

U.S. PATENT DOCUMENTS

| 5,422,105 | A | | 6/1995 | Ralph et al. |
| 5,556,620 | A | | 9/1996 | Ralph et al. |
| 5,702,697 | A | | 12/1997 | Zimmerman et al. |
| 5,888,495 | A | * | 3/1999 | Schrier ................. C07K 14/53 424/85.1 |

OTHER PUBLICATIONS

Bertram, John F.; "Analyzing Renal Glomeruli with the New Stereology"; Dept. of Anatomy and Cell Biology, University of Melbourne, Parkville, Victoria 3052, AU; (1995); 161:111-165.
Bhatnagar et al., Dev. 121: 1333-1339, 1995.
Cecchini, M.G. et al. "Role of Colony Stimulating Factor-1 in the Establishment and Regulation of Tissue Macrophages During Postnatal Development of the Mouse," Development (1994) 120, pp. 1357-1372.
Dai, Xu-Ming et al.; "Targeted Disruption of the Mouse Colony-Stimulating Factor 1 Receptor Gene Results in Osteopetrosis, Mononuclear Phagocyte Deficiency, Increased Primitive Progenitor Cell Frequencies, and Reproductive Defects"; *Blood*; 99:1 (2002) 111-120.
Draper, Elizabeth S. et al.; "Prediction of Survival for Preterm Births by Weight and Gestational Age: Retrospective Population Based Study"; British Medical Journal; vol. 319; Oct. 23, 1999; pp. 1093-1097.
Dressler, Gregory R.; "Development of the Excretory System"; Department of Pathology, University of Michigan, Ann Arbor, Michigan 48109 (2002) Chapter 18; 395-420.
Elliot, C. et al.; "Factors Affecting Foal Birth Weight in Thoroughbred Horses"; Theriogenology; 71 (2009) 683-689.
Gardner, D. S. et al.; "Factors Affecting Birth Weight in Sheep: Maternal Environment"; Reproduction; (2007); 133; 297-307.
Google search for Millipore catalog No. GF053 CSF-1, one page, available from Google search results and printed on Jun. 20, 2011.
Hayashi, Masatoshi et al.; "Elevation of Amniotic Fluid Macrophage Colony-Stimulating Factor in Normotensive Pregnancies That Delivered Small-for-Gestational-Age Infants"; *American Journal of Reproductive Immunology*; 57 (2007) 488-494.

(Continued)

*Primary Examiner* — Gyan Chandra

(74) *Attorney, Agent, or Firm* — Jones Day

(57) ABSTRACT

Methods and compositions are provided for promoting organ development in warm blooded animals, and in particular in certain aspects a premature infant or foetus. Compositions and methods are also provided for the administration of at least one colony stimulating factor-1 protein (CSF-1), precursor, variant, analogue, derivative thereof, or combinations thereof, or otherwise, at least one nucleic acid molecule encoding colony stimulating factor-1 protein (CSF-1), precursor, variant, analogue, derivative thereof, or combinations thereof.

25 Claims, 9 Drawing Sheets

(56) References Cited

OTHER PUBLICATIONS

Hinchliffe, S. A. et al.; "Human Intrauterine Renal Growth Expressed in Absolute Number of Glomeruli Assessed by the Disector Method and Cavalieri Principle"; *Laboratory Investigation*; 64:6 (1991) 777-784.

Horster, Michael F. et al.; "Embryonic Renal Epithelia: Induction, Nephrogenesis and Cell Differentation"; *Physiological Reviews*; 79:4 (Oct. 1999) 1157(3).

Hume, David A. et al.; "Detection of *c-fms* Protooncogene in Early Mouse Embryos by Whole Mount in situ Hybridization Indicates Roles for Macrophages in Tissue Remodelling"; *British Journal of Haematology*, 90 (1995) 939-942.

International Search Report and Written Opinion, dated Oct. 29, 2007, for PCT/AU2007/001372.

Keith Jr., James C. et al.; "Maternal Serum Levels of Macrophage Colony-Stimulating Factor are Associated With Adverse Pregnancy Outcome"; European Journal of Obstetrics & Gynecology and Reproductive Biology; 89 (2000) 19-25.

Kett, Michelle M. et al.; "Glomerular Dimensions in Spontaneously Hypertensive Rats: Effects of AT1 Antagonism"; Journal of Hypertension; 14:1 (1996) 107-113.

Knížetová, H. et al.; "Comparative Study of Growth Curves in Poultry"; Genetics Selection Evolution; (1995) 27, 365-375.

Lin et al. J. Mammary Gland Biol. and Neopl. 7:147-162, 2002.

Michaelson, M.D. et al. "CSF-1 Deficiency in Mice Results in Abnormal Brain Development," Development (1996) 22:9, pp. 2661-2672.

Mickle et al., Med. Clin. North Am., 2000, vol. 84(3), p. 597-607.

Millipore_GF053, product sheet, one page, printed on Jun. 20, 2011.

Murakawa, H. et al. "The Relationship Between Amniotic Fluid Macrophage Colony-Stimulating Factor and Fetal Growth," J. Reprod. Immunol. (1998) 37:2, pp. 163-170.

Pandit, Jayvardhan et al.; "Three-Dimensional Structure of Dimeric Human Recombinant Macrophage Colony-Stimulating Factor"; Science; 258:5086 (Nov. 20, 1992) 1358-1362.

Pollard, J. W. "Role of Colony-Stimulating Factor-1 in Reproduction and Development," Mol. Reprod. Dev. (1997) 46:1, pp. 54-60.

Rae, Fiona et al.; "Characterisation and Trophic Functions of Murine Embryonic Macrophages Based Upon the Use of a Csflr-EGFP Transgene Reporter"; Developmental Biology; 308 (2007) 232-246.

Rossant, Janet et al.; "Emerging Asymmetry and Embryonic Patterning in Early Mouse Development"; Developmental Cell; (Aug. 7, 2004) 155-164.

Roth, P. et al. "Colony-Stimulating Factor-1 Expression in the Human Fetus and Newborn," J. Leukoc. Biol. (1995) 58:4, pp. 432-437.

Roth, P. et al. "Colony-Stimulating Factor-1 Expression is Developmentally Regulated in the Mouse," J. Leukoc. Biol. (1996) 59:6, pp. 817-823.

Schinckel, A. P. et al.; "Analysis of Pig Growth From Birth to Sixty Days of Age"; (2003); Swine Research Report, Purdue University; pp. 57-67.

Seckl, Jonathan R. et al.; "Mechanisms of Disease: Glucocorticoids, Their Placental Metabolism and Fetal 'Programming' of Adult Pathophysiology"; Nature Clinical Practice, Endocrinology & Metabolism; 3:6 (2007) 479-488.

Sreenan et al., arch Pediatr Adolsesc Med. (1999) 153: 984-988.

Stanley, E.R. et al. "Biology and Action of Colony-Stimulating Factor-1" Mol. Reprod. Dev. (1997) 46:1, pp. 4-10.

Stoll et al., JAMA 292: 2357-2365, 2004.

Tuo, W. et al., "Colony-Stimulating Factor-1 in Conceptus and Uterine Tissues in Pigs," Biology of Reproduction (1995) 53:133-142.

\* cited by examiner

METHODS AND COMPOSITIONS FOR PROMOTING ORGAN GROWTH AND DEVELOPMENT

CROSS-REFERENCE TO RELATED APPLICATIONS

This application is a continuation of U.S. application Ser. No. 13/685,327, filed Nov. 26, 2012, which is a continuation of U.S. application Ser. No. 13/236,177, filed Sep. 19, 2011, now U.S. Pat. No. 8,338,370, which is a continuation of U.S. application Ser. No. 11/902,062 filed Sep. 18, 2007, now abandoned, which is a continuation-in-part of a PCT application PCT/AU2007/001372, filed in the Australian Receiving Office on Sep. 17, 2007, (which claims priority to Australian Provisional Application No. AU 2006905099, filed on Sep. 15, 2006, entitled "Method For Promoting Organ Development" and Australian Provisional Application No. AU 2006905156, filed Sep. 18, 2006, entitled "Method For Promoting OrganDevelopment"), and is also a continuation-in-part of International Patent Application No. PCT/AU2006/000357, filed Mar. 17, 2006, entitled "Renal Repair and Regeneration" (which claims priority to Australian Provisional Application No. AU 2005901346, filed Mar. 18, 2005, entitled "Renal Repair and Regeneration"). Each of these documents, including those in parenthesis, are incorporated herein by reference in its entirety. In addition, each of the following documents are incorporated herein by reference in its entirety:

Bertram J F (1995) Analyzing renal glomeruli with the new stereology; International Review of Cytology; 161: 111-172.

Dressier, G. R. (2002). Development of the Excretory System. Mouse Development—Patterning, Morphogenesis and Organogenesis.

J. Rossant and P. P. L. Tam. Houston, Academic Press: 395; Goldenring J (2004). Respiratory Distress Syndrome in Infants. MedlinePlus Medical Encyclopedia. [Available at http://www.nlm.nih.gov/medlineplus/ency/article/001563.htm].

Hayashi M. Zhu K. Sagesaka T. Fukasawa I. Inaba N. Elevation of amniotic fluid macrophage colony-stimulating factor in normotensive pregnancies that delivered small-for-gestational-age infants. American Journal of Reproductive Immunology. 57(6):488-94, 2007 June.

Hinchliffe, S., Sargent, P., et al. (1991). "The effect of intrauterine growth expressed in absolute number of glomeruli assessed by the "disector" method and Cavalieri principle." Lab Investigator, 64: 777-784.

Horster, M., Braun, G., et al. (1999). "Embryonic renal epithelia: Induction, nephrogenesis and cell differentiation." Physiological Reviews, 79(4): 1157-1191.

Hume, D., Monkley, S., et al. (1995). "Detection of c-fms protooncogene in early mouse embryos by whole mount in situ hybridisation indicates roles for macrophages in tissue remodelling." British Journal of Haematology, 90(4): 939-942.

Kett M M, Alcorn D, Bertram J F, Anderson W P (1996). Glomerular dimensions in spontaneously hypertensive rats: effects of ATI antagonism. Journal of Hypertension; 14: 107-113.

Keith J C Jr. Pijnenborg R. Luyten C. Spitz B. Schaub R. Van Assche F A. Maternal serum levels of macrophage colony-stimulating factor are associated with adverse pregnancy outcome. European Journal of Obstetrics, Gynecology, & Reproductive Biology, 89(1):19-25, 2000.

Wei S. Lightwood D. Ladyman H. Cross S. Neale H. Griffiths M. Adams R. Marshall D. Lawson A. McKnight A J. Stanley E R. Modulation of CSF-1-regulated post-natal development with anti-CSF-1 antibody, Immunobiology. 210(2-4):109-19, 2005.

Dai X M. Zong X H. Sylvestre V. Stanley E R. Incomplete restoration of colony-stimulating factor 1 (CSF-1) function in CSF-1-deficient Csflop/Csflop mice by transgenic expression of cell surface CSF-1. Blood, 103(3): 1114-23, 2004.

Seckl J R, Holmes M C. Mechanisms of disease: glucocorticoids, their placental metabolism and fetal 'programming' of adult pathophysiology. Nat Clin Pract Endocrinol Metab., 3(6):479-88, 2007.

Gennaro, Alfonso, Remington's Pharmaceutical Sciences, 18$^{th}$ edition, Mack Publishing Co. (1990).

University of the Sciences in Philadelphia (editor) Remington: The Science and Practice of Pharmacy 21$^{st}$ edition (2005).

Rae F, Woods K, Sasmono T, Campanale N, Taylor D, Ovchinnikov D, Grimmond S M, Hume D A, Ricardo S D, and Little M H. Characterisation and trophic functions of murine embryonic macrophages based upon the use of a CSF-1R-EGFP transgenic reporter. Developmental Biology (In Press, accepted May 24) 2007.

FIELD

THIS INVENTION relates to use of colony stimulating factor 1 (macrophage colony stimulating factor) in relation to the kidney. More particularly, this invention relates to use of colony stimulating factor 1 for treating a renal disease or condition associated with renal damage or dysfunction.

The present disclosure relates to embodiments for promoting organ development in warm blooded animals, and in particular in certain aspects a premature infant or foetus. Compositions and methods are provided for the administration of colony stimulating factor-1 protein (CSF-1), or a precursor, variant, analogue or derivative thereof, or otherwise, a nucleic acid molecule encoding colony stimulating factor-1 protein (CSF-1), or a precursor, variant, analogue or derivative thereof.

BACKGROUND

Development of the kidney is a process involving branching morphogenesis. The metanephros, or permanent kidney, is first observed at E10.5 in the mouse. Reciprocal inductive interactions between the ureteric bud (UB), an outgrowth of the Wolffian duct, and the metanephric mesenchyme (MM) result in branching of the UB to form the collecting duct system of the mature kidney and the differentiation of the mesenchyme into the glomeruli and uriniferous tubules (Saxen, 1987, Organogenesis of the kidney. Cambridge University Press., Cambridge). In both embryonic and adult kidney, most epithelial structures are surrounded by renal interstitium. Interstitial cells are responsible for the production of extracellular matrix components and development and support of the functional units of the kidney, including feedback control of the glomerular capillary blood flow.

The adult (Hume et al., 1983, J Exp Med., 158 1522-36) and embryonic mammalian renal interstitium contains resident macrophages. The phenotype and potential tissue specific function of renal macrophages, and tissue macrophages in general, is not well defined. A little is known about their growth factor production and receptor profile. The expression of Cxcr4 on renal macrophages allows them to respond to the production of Cxcl12 by the comma and S-shaped bodies of the kidney (Grone et al., 2002, JASN, 13, 957-67). Conversely, renal macrophages express Cxcl10 (IP-IO), allowing them to signal to the Cxcr3 receptor in the developing kidney mesenchyme (Grone, et al., 2002, supra).

The importance of macrophage infiltration in development is mirrored in adult tissue repair. In numerous examples of tissue repair, including models of acute damage to muscle, liver, lung, gastrointestinal tract and peripheral nervous system, infiltration by macrophages and production of macrophage-derived trophic factors appears to be absolutely essential for regeneration (Kluth, et al., 2004, Kidney International., 66 542-57).

But macrophages are the classical two-edged sword.

In systems where the damage is severe or progressive and where the damage stimulus remains, including chronic inflammation, macrophages are the dominant cell type in the inflammatory exudates and they are implicated directly in cell death and tissue damage. Indeed, conventional wisdom in both renal disease and allograft rejection has been that macrophages are responsible for damage (Eitner, et al., 1998, Transplantation, 66, 1551-7; Segerer, et al., 2003, Curr. Opin. Nephrol. Hypertens., 12, 243-9) and many therapeutic strategies have focused on ways in which to reduce macrophage recruitment and activation. A reduction in the production of chemokines involved in macrophage recruitment, proliferation and activation has been shown to be potentially beneficial not only in renal disease classically associated with immune perturbations, such as glomerulonephritis and lupus nephropathy, but also in unilateral ureteric obstruction and diabetes (Naito, et al., 1996, Mol. Med., 2, 297-312; Utsunomiya, et al., 1995, J. Diabetes Complications, 9, 292-5). However, this is not always the case (Veilhauer, et al., 2004, Kidney Blood Press. Res., 27, 226-38; Holdsworth, et al., 2000, Curr. Opin Neprhol. Hypertens., 9, 505-11). Macrophage migration inhibitory factor (MIF), while associated with renal injury in the rat, has been shown to be independent of macrophage recruitment and renal fibrosis in a unilateral ureteral obstruction (UUO) model in the mouse (Rice et al., 2004, Nephrology 9 278-287).

CSF-1 (macrophage colony-stimulating factor; M-CSF) is the major growth factor for cells of the macrophage lineage. Increased CSF1 levels are associated with renal disease and allograft rejection (Isbel, et al., 2001, Nephrol. Dial. Transplant., 16, 1638-47; Le Muer, et al., 2002, Leukoc. Biol., 72, 530-7; Le Muer, et al., 2004, Nephrol. Dial. Transplant., 19, 1862-5). CSF-1 acts on its target cells by binding to colony-stimulating factor 1 receptor (CSF-1R), a cell-surface tyrosine kinase receptor encoded by the c-fms proto-oncogene, which is expressed in macrophage and trophoblast cell lineages (Sasmono, et al., 2003, Blood, 101, 1155-1163). c-fms is critical for the proliferation, survival and differentiation of macrophages as disruption of the gene results in large depletions of macrophages in most tissues (Dai et al., 2002, Blood, 99, 111-20).

Mutation of the CSF-1 gene, such as that present in op/op mice, or blockade of CSF-1 function with either anti-CSF-1 or anti-c-fms antibodies, greatly reduces renal damage in several models including experimental glomerular nephritis, renal tubular interstitial nephritis, autoimmune nephritis and ureteral ligation (Lenda, et al., 2003, J. Immunology, 170, 3254-62; Jose, et al., 2003, Am. J. Transplant, 3, 294-300). In each of these model systems, CSF-1 is produced locally, and probably also systemically (although this is seldom measured), and the interpretation has been that CSF-1 acts to recruit and activate macrophages to cause tissue damage.

Administered granulocyte colony stimulating factor (G-CSF) has been shown to protect mouse kidneys from subsequent cisplatin damage. Cisplatin is a widely-used anticancer drug that can induce acute renal failure due to renal tubular injury. The protective effect provided by G-CSF was enhanced by CSF-1 (i.e., M-CSF; Iwasaki, et al., 2005, JASN, 16, 658). However, the administration of CSF-1 alone prior to the induction of cisplatin damage showed no protective effect.

CSF-1 has been reported to impair the progression of lipid-induced nephrotoxiocity in streptozotocin-induced diabetic rats, by modulating the recruitment of macrophages to the glomerulus (Utsunomiya, et al., 1995, supra). However, this contradicts Miyazaki, et al., 1997, Clin. Exp. Immunol., 108, 318, who showed that increased M-CSF production is associated with an increase in recruitment of macrophages to the glomerulus in lipid-induced nephrotoxicity.

In humans, renal disease is a severe and debilitating ailment that is broadly classified as "chronic" or "acute".

Chronic renal disease (CRD) refers to the gradual decline in renal function. This ultimately progresses to end stage renal disease (ESRD) when the renal filtration rate falls below 10%. CRD prevalence is rising at 6-8% per annum worldwide. Subsequently the incidence of ESRD is also increasing. Currently, the only available treatment options for ESRD are renal transplantation and dialysis. Transplantation extends survival over dialysis, but is associated with surgical morbidity and faces a shortage of viable organs. Dialysis replaces solute clearance but does not replace all renal functions, such as endocrine or metabolic functions. For those receiving dialysis treatment, the quality of life is poor and mortality rates are high (16% pa). Acute renal failure (ARF) is a common outcome in the postoperative patient, due to nephrotoxic or ischaemic insult during treatment for another condition. ARF patients receive dialysis treatment, but the lack of adjunct therapy to dialysis is thought to contribute to the high mortality rate of 50-75%. For both acute and chronic renal conditions, there is an urgent need for more advanced therapeutic approaches.

Compared to infants who have born following a normal, full term pregnancy, premature infants, particularly babies born before 32 weeks of gestation, are at a considerably greater risk of developing a number of serious health problems including, for example, renal and lung disorders.

For instance, the low birth weight and insufficient physical development of premature infants predisposes them to respiratory complications such as respiratory distress syndrome (RDS) and chronic lung disease (also known as bronchopulmonary dysplasia). RDS is associated with irregular breathing difficulties and occurs in approximately 60 to 80 percent of infants born before 28 weeks gestation, and in 15 to 30 percent of those born between 32 and 36 weeks of gestation. Treatment of such infants typically involves supplemental oxygen, but in some cases, also requires the use of a mechanical ventilator and continuous positive airway pressure. Moreover, in severe cases, treatment will additionally involve the administration of an artificial lung surfactant. While such treatments are very successful, long-term ventilator treatment is undesirable since this can lead to lung deterioration, which in turn, can lead to bronchopulmonary dysplasia.

It is also known that premature infants are born with reduced numbers of nephrons (filtration units of the kidney), an outcome that may be associated with increased risk of developing hypertension and reduced renal function following injury later in life.

Lung Development: Analogies Between Human and Mouse:

The human lung is derived from the foregut at about 4 weeks gestation and begins as a diverticulum. The lung diverticulum is covered with splanchnic mesoderm that gives rise to the tissue components of the mature adult lung such as cartilage, smooth muscle and blood vessels. Lung development is characterised by branching morphogenesis that gives rise to the primary, secondary and tertiary bronchi. The stages of foetal lung development are classified into three distinct phases, namely; the pseudoglandular, canalicular and saccular phases. Some aspects of alveolar lung development including epithelial cell differentiation begin in the canalicular phase. However, approximately 15-18% of alveoli form late in gestation, with most of the alveoli formed after birth. Shortly after birth, the surface area of the air-blood interface increases with the formation of the alveolar ducts and sacs.

Premature infants can survive with lung development in the late canalicular or early saccular phase. This is a phase when the conducting airways have stopped branching and are enlarging at their distal termini. There is a progressive loss of extracellular matrix and mesenchymal cells that separate the capillaries from the sites of alveoli. These premature infants survive without alveoli by treatment involving mechanical ventilation and the administration of an artificial lung surfactant, although, as mentioned above, they are at risk of developing bronchopulmonary dysplasia.

In mice, the lung also arises from the ventral foregut, but at approximately embryonic day 9.5 (E9.5). Subsequently, the respiratory tree develops through the pseudoglandular (E9.5-16.5), canalicular (E16.5-17.5), and saccular (E17.5-postnatal day 5) phase. While mouse and human lung development is highly analogous from an embryological point of view and while the same genes are critical in both organisms, in contrast to the human lung, alveolarisation is not complete before birth in the mouse. At birth, the mouse lungs consists of immature terminal saccules with some secondary septa, with alveolarisation and alveolar separation occurring during the during the first 1-3 postnatal weeks. The alveolar surfaces increase through the enlargement of pre-existing alveoli with formation of new alveoli.

Kidney Development: Analogies Between Humans and Mice:

The development of the kidney is highly analogous between human and mouse with respect to the embryo logical origin of the tissues involved, the morphogenetic processes and the genes regulating these processes.

In the human (as for the mouse), both the renal and genital systems originate from the intermediate mesoderm. Development of the kidney undergoes three distinct stages before resulting in the mature adult kidney. The process begins with the formation of the pronephros, then the mesonephros and finally the metanephros, after which the pronephros and mesonephros regress, and the metanephros remains to form the functional adult kidney. Metanephric development begins with the outgrowth of ureteric bud, originating from the Wollfian duct, invading the surrounding metanephric mesenchyme. The functional units within the kidney responsible for filtration of the blood, concentration of the filtrate to form urine and reclamation of water and ions are the nephrons. The formation of these functional units is referred to as nephrogenesis. Human nephrogenesis (development of kidney nephrons) is completed before birth. The number of nephrons in normal human kidneys ranges from approximately 300,000 to more than one million. After birth, the nephron number is complete and no new nephrons are able to be formed. In humans, development of the permanent kidney begins around gestational week 5. In the third trimester, 60% of nephrons are formed and continue to form until approximately 36 weeks. No new nephrons are formed after this time.

In the mouse (as with humans), there are three embryonic kidneys, the pronephros, mesonephros and metanephros, and the development of the final permanent kidney, the metanephros, begins with the outgrowth of ureteric bud, originating from the Wollfian duct, invading the surrounding metanephric mesenchyme. This occurs at around embryonic day 9-10.5 (E9-10.5) and requires inductive signals from the metanephric mesenchyme to initiate bud development. The induced mesenchyme sends reciprocal signals to induce growth and branching of the ureteric bud. Nephron formation (nephrogenesis) is induced when factors secreted by the ureteric bud cause the induction, condensation and aggregation of the mesenchyme. Each aggregate undergoes epithelialisation and then proceeds through the developmental stages of the polarised vesicle stage, the comma and the S-stage. There is continued branching with new aggregates forming at the tips, and this process continues with the induction of new nephrons. By the end of nephrogenesis, there are more than 26 terminally differentiated cell types with distinct location, morphology and function. Unlike the human, in the mouse kidney development continues in mice until around 7-10 days after birth.

Growth Factors in Kidney and Lung Development:

Growth factors, aside from their influence in cell growth, contribute greatly to many processes including cell migration, morphogenesis, differentiation and proliferation. The roles of growth factors in branching morphogenesis in the lung and nephrogenesis in the kidney are controlled by an array of inductive and inhibitory signals. The crucial roles of factors including insulin-like growth factor-I and II (IGF-I and IGF-II), hepatocyte growth factor (HGF), and epithelial growth factor (EGF) have been well established in the developing lung and kidney. It is, however, considered that there may be numerous other growth factors which play significant roles in development of the lung and kidney.

In has been found that in warm blooded animals, usings the embodiments disclosed it is possible to promote organ development (as reflected in, for some organs, an increase in organ weight), and more particularly, increased growth and/or enhanced nephrogenesis and lung maturation. It has also been found that promoting organ development and/or maturation in a warm blooded premature infant or foetus is possible.

SUMMARY OF THE INVENTION

Notwithstanding the typical association between elevated CSF-1, macrophages and tissue and organ damage, the present inventors have identified CSF-1 as having a hitherto unrealized role in supporting and promoting renal tissue repair and regeneration.

The invention is therefore broadly directed to use of CSF-1 for regenerating, repairing or otherwise treating renal cells, tissues and/or organs, and more particularly, in prophylactic or therapeutic treatment of diseases or conditions associated with renal damage and/or dysfunction.

In a particular forms, the invention relates to use of CSF-1 for treatment of acute renal damage and/or dysfunction.

In a first aspect, the invention provides a method of prophylactically or therapeutically treating a renal disease or condition in an animal including the step of administering a CSF-1 protein or an encoding nucleic acid to an animal in need of such treatment.

In one form, the method according to the first aspect may be used to suppress, ameliorate or otherwise treat an existing renal disease or condition.

In another form the method according to the first aspect may be used as prophylaxis to prevent, inhibit, suppress or otherwise protect against subsequent renal damage and/or renal failure.

Suitably, in embodiments relating to prophylactic or protective administration of CSF-1 to prevent renal damage, CSF-1 is administered in the absence of a therapeutically effective amount of G-CSF.

Preferably, the renal disease or condition is acute renal failure.

In a second aspect, the invention provides a method of regenerating, repairing or otherwise treating renal tissue in an animal including the step of administering a CSF-1 protein or an encoding nucleic acid to an animal in need of such treatment.

In a third aspect, the invention provides a method of regenerating, repairing or otherwise treating renal tissue ex vivo including the step of exposing one or more isolated renal cells, tissues or organs to a CSF-1 protein or encoding nucleic acid.

In a fourth aspect, the invention provides a method of renal transplantation, including the step of administering to the animal one or more renal cells, tissues or organs exposed ex vivo to a CSF-1 protein or encoding nucleic acid.

In a fifth aspect, the invention provides a pharmaceutical composition for use in treating a renal disease or condition, said pharmaceutical composition comprising a CSF-1 protein or an encoding nucleic acid and a pharmaceutically acceptable carrier, diluent or excipient.

Suitably, in embodiments relating to prophylactic or protective administration of CSF-1 to prevent renal damage, said pharmaceutical composition does not comprise a therapeutically effective amount of G-CSF.

It will be appreciated from the foregoing that the renal cells may be, or may include, isolated renal macrophages as well as kidney cells.

In a sixth aspect, the invention provides use of CSF-1 in the manufacture of a medicament for prophylactically or therapeutically treating a renal disease or condition in an animal.

In one embodiment, said medicament is for prophylactically or therapeutically treating acute renal failure in an animal.

In another embodiment, said medicament is for treating an existing renal disease or condition in an animal.

It will be appreciated that the present invention has broad application to animals inclusive of human and non-human mammals.

Preferably, the animal is a human.

Throughout this specification, unless the context requires otherwise, the words "comprise", "comprises" and "comprising" will be understood to imply the inclusion of a stated integer or group of integers but not the exclusion of any other integer or group of integers.

Certain embodiments disclosed provide compositions for and methods for treating complications arising from or related to low birth weight in mammals, including for example, humans, pigs, horses, dogs and other livestock. Low birth weight may be caused by premature or preterm birth or by poor foetal growth, such as intrauterine growth restriction. There are many causes of poor foetal growth, some of which include chromosomal abnormalities, placental dysfunction, placenta previa, smoking, drug or alcohol abuse, amnionitis, abruptio placentae or preeclampsia, maternal hypertension, maternal hypoxemia, maternal toxemia, polyhydramnios, urinary tract infection, malnutrion, infection, anemia, diabetes, inadequate maternal weight gain and various diseases. The compositions and methods described herein may be used to treat and/or prevent any of these causes of low birth weight and the complications. In some embodiments, the compositions and methods described herein may be used specifically to treat or prevent causes of low birth weight such as foetal alcohol syndrome, placental insufficiency, intrauterine growth retardation (IUGD), foetal growth restriction as a result of infections, genetic abnormalities such as mutations in the gene that encodes 11-β-hydroxysteroid dehydrogenase type 2, maternal hypertension, diabetes, alcohol and illicit drug abuse or inadequate maternal weight gain.

Low birth weight in babies can result in a large number of complications including immature organ growth, such as immature lungs and kidneys, respiratory distress syndrome (RDS), intraventricular hemmorhage (IVH), Patent ductus arteriosus (PDA), necrotizing enterocolitis (NEC), retinopathy of prematurity (ROP), and osteopenia. The long term adverse effects of a low birth weight include increased risk of heart disease and renal failure, increased risk of diabetes and obesity and a possible consequence on intelligence. The compositions and methods described herein may be used to treat one or more complications arising from low birth weight in mammals and may be administered prior to birth, such as to the mother or to the foetus or after birth, such as to the infant.

Certain embodiments disclosed provide methods of treating complications arising from or related to low birth weight in mammals, such as in humans, pigs, dogs, horses or other livestock, such as in premature infants, in low birth weight infants or in foetuses comprising administering to said mammals:

at least one colony stimulating factor-1 protein (CSF-1), and/or at least one precursor, variant, analogue, derivative thereof or combination thereof, or at least one nucleic acid molecule encoding said at least one colony stimulating factor-1 protein (CSF-1), and/or at least one precursor, variant, analogue, derivative thereof, or combination thereof.

Certain embodiments disclosed include methods of treating complications arising from or related to low birth weight in mammals such as in humans, pigs, horses, dogs or other livestock, such as in premature infants, in low birth weight infants or in foetuses comprising administering to said mammals:

a low birth weight complications-reducing or -limiting amount of at least one colony stimulating factor-1 protein (CSF-1), and/or at least one precursor, variant, analogue, derivative thereof, or combination thereof, or a therapeutically effective amount of at least one nucleic acid molecule encoding a low birth weight complications-reducing or -limiting amount of said at least one colony stimulating factor-1 protein (CSF-1), and/or at least one precursor, variant, analogue, derivative thereof or combination thereof.

Certain embodiments disclosed provide pharmaceutical compositions for treating, reducing or limiting complications arising from or related to low birth weight in mammals, such as in humans, pigs, horses, dogs or other livestock, such as in premature infants, in low birth weight infants or in foetuses comprising administering to said mammals:

a low birth weight complications-reducing or -limiting amount of at least one colony stimulating factor-1 protein (CSF-1), and/or at least one precursor, variant, analogue, derivative thereof or combination thereof, or a therapeutically effective amount of at least one nucleic acid molecule encoding a low birth weight complications-reducing or -limiting amount of said at least one colony stimulating factor-1 protein (CSF-1), and/or at least one precursor, variant, analogue, derivative thereof or combination thereof.

Certain embodiments disclose methods of promoting organ development and/or maturation in mammals, such as in humans, pigs, dogs, horses or other livestock, such as in premature infants, in low birth weight infants or in foetuses are provided. In certain aspects, methods of promoting organ development and/or maturation in mammals are disclosed that comprise the step of administering to the mammal such as the human, pig, horse or other livestock, such as the premature infant, low birth weight infant or foetus:

colony stimulating factor-1 protein (CSF-1), and/or a precursor, variant, analogue, derivative thereof, or combination thereof or a nucleic acid molecule encoding said colony stimulating factor-1 protein (CSF-1), and/or a precursor, variant, analogue, derivative thereof or combination thereof.

In certain aspects, methods of promoting organ development and/or maturation in mammals are disclosed that comprise the step of administering to the mammal such as the human, pig, horse, dogs or other livestock, such as the premature infant, low birth weight infant or foetus:

at least one colony stimulating factor-1 protein (CSF-1), and/or at least one precursor, variant, analogue, derivative thereof or combination thereof, or at least one nucleic acid molecule encoding said colony stimulating factor-1 protein (CSF-1), and/or at least one a precursor, variant, analogue, derivative thereof or combination thereof.

In certain aspects, the methods of promoting organ development in a premature infant, in a low birth weight infant or in a foetus disclosed comprise the step of administering to the premature infant, the low birth weight infants or the foetus:

a premature infant, a low birth weight infant or a foetus organ development-enhancing amount of at least one colony stimulating factor-1 protein (CSF-1), and/or at least one precursor, variant, analogue, derivative thereof or combination thereof, or a therapeutically effective amount of at least one nucleic acid molecule encoding a premature infant, a low birth weight infant or a foetus organ development-enhancing amount of said at least one colony stimulating factor-1 protein (CSF-1), and/or at least one precursor, variant, analogue, derivative thereof or combination thereof.

Certain embodiments disclosed provide pharmaceutical compositions for promoting organ development in a premature infant, in a low birth weight infant or in a foetus that comprise a premature infant, a low birth weight infant or a foetus organ development-enhancing amount of at least one colony stimulating factor-1 protein (CSF-1), and/or at least one precursor, variant, analogue, derivative thereof or combination thereof, or a therapeutically effective amount of at least one nucleic acid molecule encoding a premature infant, a low birth weight infant or a foetus organ development-enhancing amount of said at least one colony stimulating factor-1 protein (CSF-1), and/or at least one precursor, variant, analogue, derivative thereof or combination thereof.

In certain aspects, methods are disclosed that promote growth and/or enhance lung development and/or maturation in mammals, such as in humans, pigs, horses, dogs or other livestock, such as in premature infants, in low birth weight infants or in fetuses. In certain aspects, the methods of promoting lung growth and/or enhancing lung development and/or maturation in mammals, such as in humans, pigs, horses, dogs or other livestock, such as in premature infants, in low birth weight infants or in foetuses comprising administering to said mammals:

colony stimulating factor-1 protein (CSF-1), and/or a precursor, variant, analogue, derivative thereof or combination thereof, or a nucleic acid molecule encoding said colony stimulating factor-1 protein (CSF-1), and/or a precursor, variant, analogue, derivative thereof or combination thereof.

In certain aspects, the methods of promoting lung growth and/or enhancing lung development and/or maturation in a premature infant, in a low birth weight infant or in a foetus disclosed comprise the step of administering to the infant or foetus:

at least one colony stimulating factor-1 protein (CSF-1), and/or at least one precursor, variant, analogue, derivative thereof, or combination thereof, or at least one nucleic acid molecule encoding said at least one colony stimulating factor-1 protein (CSF-1), and/or at least one precursor, variant, analogue, derivative thereof or combination thereof.

In certain aspects, the methods of promoting lung growth and/or enhancing lung development and/or maturation in a premature infant, in a low birth weight infant or in a foetus disclosed comprise the step of administering to the infant or foetus:

a premature infant, a low birth weight infant or a foetus lung growth promoting and/or lung development and/or maturation-enhancing amount of at least one colony stimulating factor-1 protein (CSF-1), and/or at least one precursor, variant, analogue, derivative thereof or combination thereof, or a therapeutically effective amount of at least one nucleic acid molecule encoding a premature infant, a low birth weight infant or a foetus lung growth promoting and/or lung development and/or maturation-enhancing amount of said at least one colony stimulating factor-1 protein (CSF-1), and/or at least one precursor, variant, analogue, derivative thereof or combination thereof.

Certain embodiments disclosed provide pharmaceutical compositions for promoting lung growth and/or enhancing lung development and/or maturation in a premature infant, in a low birth weight infant or in a foetus that comprise a premature infant, a low birth weight infant or a foetus lung growth promoting and/or lung development and/or maturation-enhancing amount of at least one colony stimulating factor-1 protein (CSF-1), and/or at least one precursor, variant, analogue, derivative thereof or combination thereof, or a therapeutically effective amount of at least one nucleic acid molecule encoding a premature infant, a low birth weight infant or a foetus lung growth promoting and/or lung development and/or maturation-enhancing amount of said at least one colony stimulating factor-1 protein (CSF-1), and/or at least one precursor, variant, analogue, derivative thereof or combination thereof.

In certain embodiments, methods of promoting growth, maturation and/or enhancing kidney development in mammals, such as in humans, pigs, horses, dogs or other livestock, such as in premature infants, in low birth weight infants or in foetuses. In certain aspects the methods of promoting growth, maturation and/or enhancing kidney development in mammals, such as in humans, pigs, horses, dogs or other livestock, such as in premature infants, in low birth weight infants or in foetuses comprising administering to said mammals:

colony stimulating factor-1 protein (CSF-1), and/or a precursor, variant, analogue, derivative thereof or combination thereof, or a nucleic acid molecule encoding said colony stimulating factor-1 protein (CSF-1), and/or a precursor, variant, analogue, derivative thereof or combination thereof.

In certain aspects the methods of promoting growth, maturation and/or enhancing kidney development in a premature infant, in a low birth weight infant or in a foetus comprise the step of administering to the infant or foetus;

at least one colony stimulating factor-1 protein (CSF-1), and/or at least one precursor, variant, analogue, derivative thereof, or combination thereof, or at least one nucleic acid molecule encoding said colony stimulating factor-1 protein (CSF-1), and/or at least one precursor, variant, analogue, derivative thereof or combination thereof.

In certain aspects, the methods of growth, maturation and/or enhancing kidney development in a premature infant, in a low birth weight infant or in a foetus disclosed comprise the step of administering to the infant or foetus:

a premature infant, a low birth weight infant or a foetus kidney growth maturation and/or development-enhancing amount of at least one colony stimulating factor-1 protein (CSF-1), and/or a precursor, variant, analogue, derivative thereof or combination thereof, or a therapeutically effective amount of at least one nucleic acid molecule encoding a premature infant, a low birth weight infant or a foetus kidney growth maturation and/or development-enhancing amount of said at least one colony stimulating factor-1 protein (CSF-1), and/or at least one precursor, variant, analogue, derivative thereof or combination thereof.

Certain embodiments disclosed provide pharmaceutical compositions for promoting growth, maturation and/or enhancing kidney development in a premature infant, in a low birth weight infant or in a foetus that comprise a premature infant, a low birth weight infant or a foetus kidney growth maturation and/or development-enhancing amount of at least one colony stimulating factor-1 protein (CSF-1), and/or at least one precursor, variant, analogue, derivative thereof or combination thereof, or a therapeutically effective amount of at least one nucleic acid molecule encoding a premature infant, a low birth weight infant or a foetus kidney growth maturation and/or development-enhancing amount of at least one said colony stimulating factor-1 protein (CSF-1), and/or at least one precursor, variant, analogue, derivative thereof or combination thereof.

In certain aspects, methods are disclosed that promote growth and/or enhance bone development and/or maturation in mammals, such as in humans, pigs, horses, dogs or other livestock, such as in premature infants, in low birth weight infants or in foetuses. In certain aspects, the methods of promoting bone growth and/or enhancing bone development and/or maturation in mammals, such as in humans, pigs, horses, dogs or other livestock, such as in premature infants, in low birth weight infants or in foetuses comprising administering to said mammals:

colony stimulating factor-1 protein (CSF-1), and/or a precursor, variant, analogue, derivative thereof or combination thereof or a nucleic acid molecule encoding said colony stimulating factor-1 protein (CSF-1), and/or a precursor, variant, analogue, derivative thereof or combination.

In certain aspects, the methods of promoting bone growth and/or enhancing bone development and/or maturation in a premature infant, in a low birth weight infant or in a foetus disclosed comprise the step of administering to the infant or foetus:

at least one colony stimulating factor-1 protein (CSF-1), and/or at least one precursor, variant, analogue, derivative thereof or combinations thereof or at least one nucleic acid molecule encoding said at least one colony stimulating factor-1 protein (CSF-1), at least one precursor, at least one variant, at least one analogue, at least one derivative thereof or combinations thereof.

In certain aspects, the methods of promoting bone growth and/or enhancing bone development and/or maturation in a premature infant, in a low birth weight infant or in a foetus disclosed comprise the step of administering to the infant or foetus:

a premature infant, a low birth weight infant or a foetus bone growth promoting and/or bone development and/or maturation-enhancing amount of at least one colony stimulating factor-1 protein (CSF-1), and/or at least one precursor, variant, analogue, derivative thereof or combination thereof or a therapeutically effective amount of at least one nucleic acid molecule encoding a premature infant, a low birth weight infant or a foetus bone growth promoting and/or bone development and/or maturation-enhancing amount of said at least one colony stimulating factor-1 protein (CSF-1), and/or at least one precursor, variant, analogue, derivative thereof or combination thereof.

Certain embodiments disclosed provide pharmaceutical compositions for promoting bone growth and/or enhancing bone development and/or maturation in a premature infant, in a low birth weight infant or in a foetus that comprise a premature infant, a low birth weight infant or a foetus bone growth promoting and/or bone development and/or maturation-enhancing amount of at least one colony stimulating factor-1 protein (CSF-1), and/or a precursor, variant, analogue, derivative thereof or combination thereof, or a therapeutically effective amount of at least one nucleic acid molecule encoding a premature infant, a low birth weight infant or a foetus bone growth promoting and/or bone development and/or maturation-enhancing amount of said at least one colony stimulating factor-1 protein (CSF-1), and/or at least one precursor, variant, analogue, derivative thereof or combination thereof.

DETAILED DESCRIPTION

Figure 1:
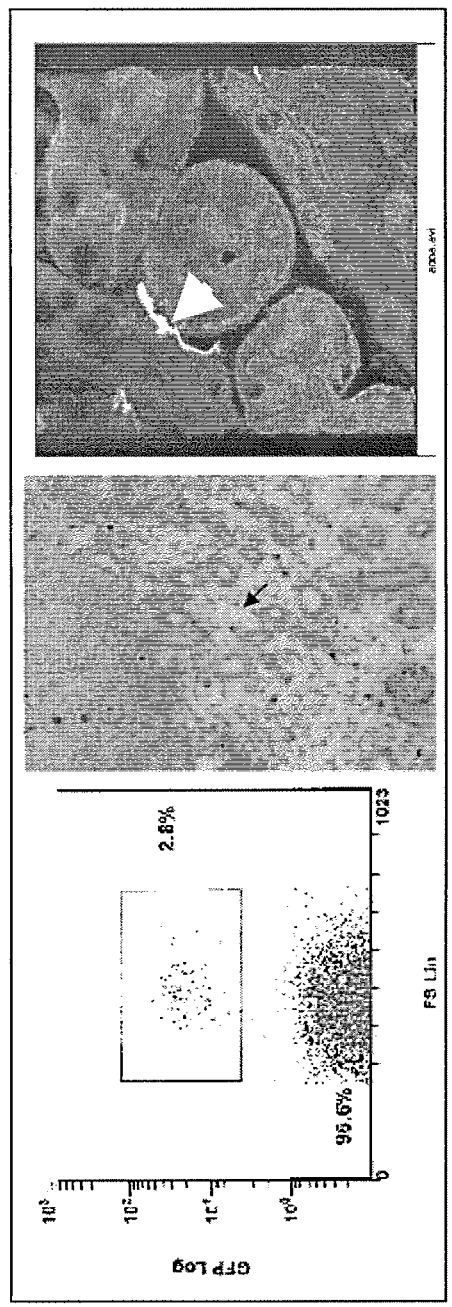
FIG. 1. Resident renal macrophages. Left panel: FACS profile of GFP+ cells isolated from embryonic day 15.5 kidneys of c-fms-EGFP transgenic mice represent 2.8% of total cells. Middle panel: RNA section in situ hybridisation of macrophage-specific outlier shows punctate expression within the interstitial macrophages of the kidney. Right panel: Two colour confocal image of a renal macrophage (arrowhead) between renal proximal tubules.

While CSF-1 has previously been observed to assist G-CSF in preventing renal damage (i.e., reno-protection) and to modulate recruitment of macrophages to the glomerulus of rats having lipid-induced nephrotoxocity (although its precise role remains controversial), the present invention has arisen, at least in part, from the surprising observation that CSF-1 stimulates macrophages to promote growth, regeneration and/or repair of the kidney. By extension, the production of CSF-1 in renal disease forms part of a protective/regenerative response that fails only when there is ongoing tissue damage elicited by a separate causal agent. Thus, it proposed that treatment with CSF-1 could provide a paradoxical and unexpected approach to therapy for renal diseases and/or conditions.

As used herein "CSF-1 protein" includes and encompasses any CSF-1 protein (also known as macrophage colony stimulating factor or M-CSF) of mammalian origin, including any biologically active fragment of a CSF-1 protein It will be appreciated that the invention also contemplates use of any of a number of modified and/or fragmentary forms of CSF-1.

For example, U.S. Pat. No. 6,322,779 describes an isolated recombinant, dimeric CSF-1 is which is unglycosylated and which can be produced essentially endotoxin and pyrogen-free.

In particular, several C-terminally truncated fragments of CSF-1 have been described which retain biological activity.

By way of example, reference is made to U.S. Pat. No. 6,204,020 and U.S. Pat. No. 6,146,851 which describe various carboxy-truncated forms of CSF-1 protein and their encoding nucleic acids.

A biologically active CSF-1 dimer is described in U.S. Pat. No. 5,861,150, wherein at least one of the CSF-1 monomers has one or more amino acid substitutions together with a carboxy truncation.

U.S. Pat. No. 5,672,343 sets forth a CSF-1 protein consisting of amino acids 4-522 of the 536 amino acid CSF-1 sequence and fragments of CSF-1 comprising truncations at various positions C-terminal of residue 149.

The invention also contemplates use of any other molecule that has CSF-1 agonist activity, including but not limited to any molecule capable of binding, dimerizing and/or activating the cognate CSF-1 receptor (CSF-1R or c-fms).

CSF-1 protein may be in native form purified from a natural source, including but not limited to human urine. An example of such a product is Mirimostim™ from Mitsubishi Pharma.

CSF-1 may also be in recombinant or chemical synthetic form.

For example, the present invention contemplates chemical synthesis of CSF-1 protein, inclusive of solid phase and solution phase synthesis. Such methods are well known in the art, although reference is made to examples of chemical synthesis techniques as provided in Chapter 9 of SYNTHETIC VACCINES Ed. Nicholson (Blackwell Scientific Publications) and Chapter 15 of CURRENT PROTOCOLS IN PROTEIN SCIENCE, Eds., Coligan, et al., (John Wiley & Sons, Inc., NY, USA, 1995-2001).

The invention also contemplates recombinant DNA technology as a means of producing recombinant CSF-1, including but not limited to, standard protocols as for example described in Sambrook, et al., MOLECULAR CLONING. A Laboratory Manual, (Cold Spring Harbor Press, 1989), in particular Sections 16 and 17; CURRENT PROTOCOLS IN MOLECULAR BIOLOGY, Eds., Ausubel, et al., (John Wiley & Sons, Inc., NY, USA, 1995-2001), in particular Chapters 10 and 16; and CURRENT PROTOCOLS IN PROTEIN SCIENCE, Eds., Coligan, et al., (John Wiley & Sons, Inc., NY, USA, 1995-2001, in particular Chapters 1, 5, and 6).

In one embodiment, the CSF-1 protein is bacterially-expressed, non-glycosylated human recombinant CSF-1.

However, use of glycosylated forms of CSF-1 (such as produced by mammalian cell expression systems) are also suitable for use according to the invention.

Preferably, the CSF-1 protein consists of a C-terminal 150 amino acid fragment of CSF-1 protein.

The invention also contemplates CSF-1 protein "derivatives", which have been altered, for example by addition, conjugation or complexing with other chemical moieties or by post-translational modification techniques, as are well understood in the art.

By way of example only, the invention contemplates derivatives of CSF-1 such as, but not limited to, chemical modification of side chains (e.g., pegylation of nucleophilic groups such as lysyl ε-amino groups or sulphydryl oxidation by performic acid oxidation to cysteic acid), chemical modification of the C-terminus (e.g., carbodiimide activation via O-acylisourea formation followed by subsequent derivitization to a corresponding amide), chemical modification of the N-terminus (e.g., acylation with acetic or succinic anhydride), incorporation of non-natural amino acids and/or their derivatives during protein synthesis and the use of cross-linkers, labels (e.g., fluorochromes, radionuclides, biotin) and other adducts.

Other CSF-1 derivatives may comprise additional amino acid sequences such as fusion partner sequences. Fusion partner sequences, by way of example, assist in protein purification and/or identification. For instance, these include "epitope tags" such as c-myc, FLAG and influenza haemagglutinin tags, polyhistidine (e.g., HIS6), maltose binding protein, green fluorescent protein (GFP), immunoglobulin heavy chain Fc portion and glutathione S-transferase (GST), although without limitation thereto.

For the purposes of fusion polypeptide purification by affinity chromatography, relevant matrices for affinity chromatography are antibody, protein A- or G-, glutathione-, amylose-, and nickel- or cobalt-conjugated resins respectively. Many such matrices are available in "kit" form, such as the QIAexpress™ system (Qiagen) useful with (HIS6) fusion partners and the Pharmacia GST purification system.

Isolated Nucleic Acids and Expression Constructs

It will be appreciated from the foregoing and also from renal treatment methods and compositions to be described in more detail hereinafter, that the invention also provides use of an isolated nucleic acid encoding a CSF-1 protein.

The term "nucleic acid" as used herein designates single- or double-stranded mRNA, RNA, cRNA, RNAi and DNA inclusive of cDNA and genomic DNA and DNA-RNA hybrids. Nucleic acids may also be conjugated with fluorochromes, enzymes and peptides as are well known in the art.

The invention also contemplates variant CSF-1 nucleic acids having one or more codon sequences altered by taking advantage of codon sequence redundancy.

A particular example of a variant CSF-1 nucleic acid is optimization of a nucleic acid sequence according to codon usage, as is well known in the art. This can effectively "tailor" a nucleic acid for optimal expression in a particular organism, or cells thereof, where preferential codon usage has been established.

In certain embodiments, said isolated CSF-1 nucleic acid may be present in an expression construct, wherein the said isolated nucleic acid is operably linked or connected to one or more regulatory sequences in an expression vector.

In one particular embodiment, the expression construct is suitable for bacterial expression of CSF-1 protein in bacteria such as *E. coli*.

In another particular embodiment, the expression construct is for expression in one or more mammalian cells, tissues or organs in vitro or in vivo.

According to this embodiment, the mammalian cells, tissues or organs include kidney cells, resident renal macrophages and/or bone marrow-derived macrophages.

Accordingly, an "expression vector" may be either a self-replicating extra-chromosomal vector such as a plasmid, or a vector that integrates into a host genome, inclusive of vectors of viral origin such as adenovirus, lentivirus, poxvirus and flavivirus vectors as are well known in the art.

By "operably linked or connected" is meant that said regulatory nucleotide sequence(s) is/are positioned relative to the recombinant nucleic acid of the invention to initiate, control, regulate or otherwise direct transcription and/or other processes associated with expression of said nucleic acid.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, splice donor/acceptor sequences and enhancer or activator sequences.

Constitutive promoters (such as CMV, SV40 and human elongation factor promoters) and inducible/repressible promoters (such as tet-repressible promoters and IPTG-, alcohol-, metallothionine- or ecdysone-inducible promoters) are well known in the art and are contemplated by the invention, as are tissue-specific promoters such as α-crystallin promoters. It will also be appreciated that promoters may be hybrid promoters that combine elements of more than one promoter (such as SRα promoter).

The expression construct may also include a fusion partner (typically provided by the expression vector) so that the recombinant CSF-1 protein is expressed as a fusion polypeptide with said fusion partner, as hereinbefore described.

Expression constructs may also include a selection marker nucleic acid that confers transformed host cell resistance to a selection agent. Selection markers useful for the purposes of selection of transformed bacteria include bla, kanR and tetR while transformed eukaryotic cells may be selected by markers such as hygromycin, G418 and puromycin, although without limitation thereto.

Expression constructs may be introduced into cells or tissues by any of a number of well known methods typically referred to as "transfection" "transduction", "transformation" and the like. Non-limiting examples of such methods include transformation by heat shock, electroporation, DEAE-Dextran transfection, microinjection, liposome-mediated transfection (e.g. lipofectamine, lipofectin), calcium phosphate precipitated transfection, viral transformation, protoplast fusion, microparticle bombardment and the like.

Pharmaceutical Compositions and Methods of Treatment

A variety of diseases and conditions can damage kidney parenchyma, such as atheroembolic disease, renal vein thrombosis, renal artery embolism, thrombosis, diabetic nephropathy, glomerulonephritis of various etiology, toxic nephrosis, and pyelonephritis. As a result of the damage, renal failure, whether arising from an acute or chronic decline in renal function, is a grave condition that can result in substantial or complete failure of the filtration, reabsorption, endocrine, and homeostatic functions of the kidney.

In one aspect, the invention therefore provides a method of prophylactically or therapeutically treating a renal disease or condition in an animal, such as by regenerating renal tissue in vivo in the animal, by administering a CSF-1 protein, or an expression construct encoding a CSF-1 protein, to the animal.

It will be appreciated that CSF-1 may be administered alone or together with one or more other therapeutic agents that facilitate or assist in treating the renal disease or condition.

A non-limiting example of such a therapeutic agent includes immunosuppressive agents {e.g. cyclosporine) and antibiotics (e.g. amoxicillin, cephalosporins, levofloxacin and ciprofloxacin).

In one particular embodiment relating to prophylactic treatment, said one or more other therapeutic agents is not G-CSF.

It will also be appreciated that the invention contemplates combination with other treatments such as dialysis, surgery and transplantation.

In a preferred embodiment, the invention provides a method of treating an existing renal disease or condition in an animal.

The term "renal disease or condition" broadly includes and encompasses both acute and chronic renal failure.

By "acute renal failure" is meant sudden loss of the ability of the kidneys to excrete wastes, concentrate urine, and/or conserve electrolytes.

Acute renal failure occurs relatively rapidly, such as in the postoperative patient, due to nephrotoxic or ischaemic insult during treatment for another condition.

A more comprehensive review and discussion of acute renal failure can be found in Lameire, et al., 2006, JASN, 17, 923, and Xue, et al., 2006, JASN, February 22.

By "chronic renal disease" is meant a gradual decline in renal function which ultimately progresses to end stage renal disease (ESRD) where the renal filtration rate falls below 10%.

In one embodiment, the chronic renal disease is not lipid-induced nephrotoxocity.

In a preferred embodiment, the invention relates to treatment of acute renal failure, such as where rapid renal repair and/or regeneration is required.

However, it will be appreciated that immediate delivery of CSF-1 in vivo may also be useful in ongoing treatment of chronic renal disease.

In an alternative, less preferred embodiment, the invention provides use of CSF-1 for prophylactic administration to an animal to prevent, inhibit, suppress or otherwise protect against subsequent renal damage and/or renal failure.

Suitably, according to such an embodiment CSF-1 is administered to the animal in the absence of a therapeutically effective amount of G-CSF.

As used herein, an example of a therapeutically effective amount of G-CSF is an amount which is sufficient to protect against subsequent renal failure.

An example of a therapeutically effective amount of G-CSF is 250 µg/kg, such as described in Iwasaki, et al., 2005, supra.

Preferably, CSF-1 is administered in the absence of G-CSF.

Thus, a therapeutic agent administered according to the invention may "consist of CSF-1 or "consist essentially of CSF-1.

By "consist essentially of is meant that CSF-1 is the major, therapeutically active agent administered to said animal.

For example, CSF-1 provides, accounts for, or constitutes at least 60%, preferably at least 70%, more preferably at least 80% and advantageously at least 85%, 90% or 95-99% of the therapeutic activity administered to the animal.

In particular embodiments, CSF-1 is delivered as a pharmaceutical composition that further comprises a pharmaceutically acceptable carrier, diluent or excipient.

In general terms, by "pharmaceutically-acceptable carrier, diluent or excipient is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co., NJ, USA, 1991) which is incorporated herein by reference.

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of proteinaceous and nucleic acid molecules.

Dosage forms include tablets, dispersions, suspensions, injections, solutions, syrups, troches, capsules, suppositories, aerosols, transdermal patches and the like.

These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of CSF-1 protein or an expression construct encoding same, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

Preferably, pharmaceutical compositions are deliverable directly to the kidney in a manner which avoids or lessens the likelihood of CSF-1-induced side effects that might result from systemic delivery.

In this regard, a CSF-1 reservoir may be utilized which is transplantable into an animal, preferably at a site in proximity to the kidney, which delivers a controlled, metered dosage of CSF-1 over time.

In one embodiment, CSF-1 may be delivered by an implanted osmotic pump that delivers CSF-1 to a location proximal to the kidney and/or into the renal blood supply such as via the renal artery.

In another embodiment, microsphere-based delivery may be achieved by reconstituting CSF-1 in solvent including distilled water and chitosan and combining this solution with polylactic-co-glycolic acid in an aqueous solution so that an emulsion is formed by ultrasonic treatment. The membrane is permeable to CSF-1 and biocompatible and biodegradable with human kidney tissue without forming toxic waste products. Release can be controlled by the biodegradation kinetics of the chitosan used. For example, recombinant human colony stimulating factor 1 (rhCSF-1) was delivered in chitosan microcapsules that were injected locally into injured mouse brain so that CSF-1 was constitutively released for different lengths of time to enhance survival of neurons in injured brain (Berezovskaya, et al., 1996, Acta Neuropathol., 92, 479-86).

Another particular, non-limiting example of CSF-1 protein delivery technology is provided in United States Patent Application 20040191215.

In one embodiment, CSF-1 may be provided in a macroporous reservoir comprising CSF-1 in a biologically and chemically inert particle having interconnected pores. The pores are open to the particle surface for communication between the exterior of the particle and the internal pore spaces. Examples of particles for formation of such macroporous reservoirs are described, for example, in U.S. Pat. No. 5,135,740.

In another embodiment, CSF-1 reservoir may be provided by way of a microcapsule and/or microparticle, having CSF-1 contained or dispersed therein. Both microcapsules and microparticles are well known in the pharmaceutical and drug delivery industries (see, for example, Baker, R. W., CONTROLLED RELEASE OF BIOLOGICALLY ACTIVE AGENTS, John Wiley & Sons, NY, 1987; Ranade V. and Hollinger, M., DRUG DELIVERY SYSTEMS, CRC Press, 1996).

A microcapsule would typically comprise a reservoir or bolus of CSF-1 contained within a polymer membrane shell.

A microparticle would typically be a monolithic system where CSF-1 is dispersed throughout the particle.

Specific procedures for encapsulation of biologically active agents which may be relevant to CSF-1 are disclosed in U.S. Pat. No. 4,675,189 and U.S. patent application No. 20010033868.

In yet another embodiment, the invention contemplates a polymer gel formulation comprising CSF-1. An example of a polymer for use in such a gel formulation is a polyoxyethylene-polyoxypropylene block copolymer (Pluronic.RTM.). These copolymers exhibit reverse thermal gelation behavior, have good drug release characteristics, and have a low toxicity. The copolymers gel as a function of temperature and polymer concentration, where an aqueous solution gels as the solution is warmed. The gel has a low viscosity at room temperature, but at a typical body temperature the viscosity increases.

Other suitable polymers for preparation of CSF-1 delivery reservoirs include, but are not limited to collagen (Pieper et al., 2000, Biomaterials, 21, 1689-1699); fibrin (Grassi, et. al., 2002, J. Biomed. Mater. Res., 60, 607-612); yaupon gels (Ramamurthi, et al., 2002, J. Biomed. Mater. Res., 60, 196-205); derivatized dextrans (Letourneur, et al., 2002, J. Biomed. Mater. Res., 60, 94-100); heparin alginate (Laham, et al., 1999, Circulation, 100, 1865-1871); alginate (U.S. Pat. Nos. 6,238,705 & 6,096,344); and chochleates (U.S. Pat. No. 6,403,056).

In yet another embodiment, CSF-1 may be delivered by way of a liposome.

Liposomes are typically, although not exclusively, spherical lipid vesicles, ranging in size from 0.01 to 10 microns, and consist of one or more lipid bilayer encapsulating an aqueous space. A variety of amphipathic lipids are used to form the bilayer, such as phospholipids, as for example described in U.S. Pat. No. 5,013,556. The lipid molecules are generally arranged with their polar head groups toward the water phase and the hydrophobic hydrocarbon tails adjacent to one another in the bilayer, thus forming closed, concentric bimolecular lipid leaflets separating aqueous compartment.

As previously described, the invention also contemplates delivery of an expression construct that comprises an isolated nucleic acid encoding CSF-1 protein.

For example, the invention contemplates intravenous injection of a plasmid DNA expression construct comprising a CMV promoter operably linked or connected to a CSF-1 nucleotide sequence using a procedure such as described for delivery of hepatocyte growth factor to renal glomeruli of mice (Dai, et al., 2004, J Am Soc Nephrol., 15, 2637-47).

In another example, the invention contemplates transduction of primary cultures of isolated macrophages with a CSF-1 expression construct (for increased expression). Macrophages are then injected systemically or into the renal artery and will localize to the damaged kidney, as has been demonstrated with respect to IL-IO in rats with nephritis (Wilson, et al., 2002, Mol Ther., 6, 710-7).

In yet another example, the invention contemplates therapeutic delivery of a recombinant viral vector encoding CSF-1 injected intravenously into renal disease patients Delivery of CSF-1 expression constructs may be facilitated by use of appropriate delivery agents.

Biodegradable hydrogels may be formulated from cationized gelatin prepared through aminization containing plasmid DNA including a human CSF-1 nucleotide sequence operably linked or connected to a promoter operable in a mammalian cell (e.g., a CMV promoter).

Similar approaches using microspheres and hydrogels (containing DNA constructs encoding recombinant matrix metalloproteinases) have shown that injection into the renal subcapsule of C57BL/6 mice which have had streptozotocin-induced diabetes, showed promise as a prophylactic treatment of kidney fibrolysis and dysfunction in the STZ-induced diabetic mouse model. (Aoyama, et al., 2003, Tissue Eng., 9, 1289).

The invention also provides a method of regenerating, repairing or otherwise treating renal tissue ex vivo for transplantation into an animal, by administering a CSF-1 protein to one or more kidney cells, tissues or organs in vitro prior to transplantation.

As used herein, "transplantation" includes and encompasses transplantation of autologous and heterologous cells, tissues and organs, as understood in the art.

With improved surgical techniques and medical management of rejection, renal transplantation has become the treatment of choice for chronic and end-stage renal disease (ESRD).

The use of immunosuppressive agents such as cyclosporine, OKT3, and FK506 has resulted in a 1-year survival rate for mismatched renal grafts of 80%. A 90% 1-year graft survival rate has been reported with non-identical grafts from living related donors and a 95% 1-year success rate for grafts with identical human lymphocyte antigen. The half-life of grafts from living related donors varies from 13-24 years. Other medical managements have further extended the functional life of renal transplants while ensuring a better quality of life for the transplant recipient.

Surgical techniques for transplantation were recently advanced with the use of laparoscopic surgical techniques. The frequency of left kidney harvesting via a laparoscopic approach has resulted in more frequent transplantation of kidneys with multiple renal arteries.

The invention therefore contemplates treatment of whole kidney or isolated kidney tissue in vitro, such as by soaking or perfusing with CSF-1, to thereby facilitate the effectiveness of transplantation to a recipient. The CSF-1 treatment may further comprise other agents such as immunosuppressants (e.g., OKT3, cyclosporine or FK506), growth factors and/or cytokines other than CSF-1 that suppress rejection and/or assist renal regeneration and/or repair (e.g., Ccl and Cxcl).

In a particular embodiment, the invention contemplates enhancing growth of renal progenitor or stem cells (once committed to a renal fate) by addition of CSF-1 to culture before injection into the renal capsule.

It will also be appreciated that resident, renal macrophages may be used therapeutically.

Although not wishing to be bound by any particular theory, it is possible that CSF-1 acts to induce renal macrophages to produce soluble factors that promote renal cell growth and development.

Examples of such factors include the chemokines within the Ccl and Cxcl families. The expression of receptors for Ccl and Cxcl chemokines on renal cells, including podocytes and collecting duct cells (Huber, et al., 2002, J Immunol., 168, 6244-52.) suggests that these ligands can signal to the kidney itself rather than simply playing a role in monocyte attraction Therefore, the invention contemplates delivery of isolated renal macrophages to renal tissue to thereby promote CSF-1-mediated repair and regeneration of renal tissue.

Resident renal macrophages may be readily isolated by way of surface markers such as c-fins, class II MHC, CD83, CD 14 and/or CD86 by cell isolation methods well known in the art (e.g., by FACS sorting or by magnetic bead enrichment).

While in preferred forms the invention provides methods of treatment of renal diseases or conditions in humans, the invention also contemplates veterinary treatments of non-human animals such as poultry, livestock (e.g., cattle, horses, goats and sheep), performance animals (e.g., racehorses including sires and broodmares) and domestic animals, although without limitation thereto.

So that preferred forms of the invention may be better understood and put into practical effect, reference is made to the following non-limiting examples.

In general, because of the strong similarities between all placental mammals in terms of organogenesis, the mouse provides an excellent predictive model for organogenesis in humans, pigs, horses, dogs and other placental mammals.

Growth factor known as colony stimulating factor-1 protein (CSF-1) (also known as macrophage colony stimulating factor (M-CSF)) controls the survival, proliferation and differentiation of cells of the monocyte/macrophage lineage, and acts by binding to the CSF-1 receptor (CSF-1R), a cell-surface tyrosine kinase receptor encoded by the c-fms proto-oncogene. Previous studies have shown that c-fms mRNA is found in the placenta, localised to cells of a macrophage specific lineage (Hume, Monkley et al., 1995). The present embodiments relate to and elucidate the role(s) that CSF-1 has in embryonic development. The applicants have found, surprisingly, that in newborn mice, CSF-1 was able to treat complications arising from or related to low birth weight, to promote organ development, and more particularly, increased growth and/or enhanced lung maturation and nephrogenesis in the kidney and increased bone growth and/or enhanced bone maturation in co-occurrence with an overall increase in size and body weight. Lung and kidney development is incomplete in newborn mice, newborn mice, therefore, provide a useful model for lung and kidney development in the human foetus and premature infants. In addition, newborn mice undergo bone and cartilage remodelling and growth postnatally. Thus, as disclosed herein the administration of CSF-1 to premature infants and pregnant mothers at risk of premature birth (or for whom premature birth is desirable) may permit treatment and/or prevention of diseases and conditions associated with underdeveloped organs such as the lungs and kidneys and bone formation.

In certain embodiments, based on studies conducted to elucidate what role(s) CSF-1 might have in embryonic development, the present applicants surprisingly found that in certain embodiments in newborn mice, CSF-1 was able to promote organ development (as reflected in, for some organs, an increase in organ weight), and more particularly, increased growth and/or enhanced nephrogenesis and lung maturation.

In certain embodiments, methods of promoting organ development and/or maturation in a premature infant or foetus, the methods comprising the step of administering to the infant or foetus;

colony stimulating factor-1 protein (CSF-1), or a precursor, variant, analogue or derivative thereof, or a nucleic acid molecule encoding said colony stimulating factor-1 protein (CSF-1), or a precursor, variant, analogue or derivative thereof.

The methods disclosed herein may be used to treat complications arising from or related to low birth weight, to promote the development of one or more organs such as, but not limited to, the lung, kidney, brain, eye and organs of the gastrointestinal (G.I.) tract, in certain aspects in particular the small intestine, and may be used to promote bone growth and development in mammals, such as humans, pigs, horses, dogs and other livestock, such as in premature infants or in foetuses. The organ development that may be achieved by the method disclosed herein can result in cell growth and cell differentiation so as to cause organ maturation (e.g. in terms of organ structure and function) towards that of infants born following a normal, full-term pregnancy and foetal development. The premature infant or foetus treated in accordance with certain embodiments may thereby avoid or defer, for example, developing hypertension and/or reduced renal function following injury later in life, respiratory distress syndrome (RDS) and bronchopulmonary dysplasia, intraventricular hemmorhage and neural development disorders that can lead to learning problems, behavioural problems and cerebral palsy, retinopathy due to abnormal growth of blood vessels, and hearing loss.

In certain embodiments, the methods involve the administration of CSF-1, at least one nucleic acid encoding CSF-1, or combinations thereof. In certain preferred embodiments, the methods disclosed involve the administration of human CSF-1, a least one nucleic acid encoding human CSF-1, or combinations thereof. However, it is also suitable in certain embodiments to administer a precursor, variant, analogue or derivative of CSF-1, at least one nucleic acid encoding same, or combinations thereof. In certain aspects it is preferred to administer, at least one precursor, at least one variant, at least one analogue, at least one derivative of human CSF-1, at least one nucleic acid encoding same, or combinations thereof.

The term "precursor" is to be understood to refer to any molecule that is converted or metabolised within the body to CSF-1. Thus, one example of a suitable CSF-1 precursor is an immature CSF-1 comprising its native, or a heterologous, secretory signal, which can be processed by proteolytic cleavage to produce CSF-1 (i.e., mature CSF-1).

The term "variant" is to be understood to refer to an isoform of CSF-1 encoded by, for example, an allelic variant.

The term "analogue" is to be understood to refer to any molecule that differs from CSF-1 but retains similarity, or substantial similarity, in biological function of CSF-1, in particular the ability to promote organ development. In certain aspects, an analogue may have substantial overall structural similarity with CSF-1 or only structural similarity with one or more regions or domains of CSF-1 responsible for its biological function. Typically, an analogue of CSF-1 will be provided by, or be the result of, the addition of one or more amino acids to the amino acid sequence of CSF-1, deletion of one or more amino acids from the amino acid sequence of CSF-1, and/or substitution of one or more amino acids of the amino acid sequence of CSF-1, and/or combinations thereof. In certain aspects, inversion of amino acids and other mutational changes that result in the alteration of the amino acid sequence are also encompassed. Such an analogue may be prepared by introducing nucleotide changes into a nucleic acid molecule such that the desired amino acid changes are achieved upon expression of the mutagenised nucleic acid molecule, or by otherwise synthesising an amino acid sequence incorporating the desired amino acid changes. The substitution of an amino acid may involve conservative or non-conservative amino acid substitution. By conservative amino acid substitution, it is meant that an amino acid residue is replaced with another amino acid having similar, or substantially similar, characteristics and which does not substantially alter the desired biological function of the protein. Exemplary conservative amino acid substitutions are provided in Table 1 below. In certain aspects, particular conservative substitutions envisaged are: G, A, V, I, L, M; D, E, N, Q; S, C, T; K, R, H; and P, N-α-alkylamino acids. In certain aspects, conservative amino acid substitutions may be selected on the basis that they do not have any substantial effect on (a) the structure of the peptide backbone in the region of the substitution, (b) the charge or hydrophobicity of the protein at the site of substitution, (c) the bulk of the side chain at the site of substitution, and/or combinations thereof.

TABLE 1

Exemplary conservative amino acid substitutions

| | Conservative Substitutions |
|---|---|
| Ala | Val*, Leu, Ile |
| Arg | Lys*, Gln, Asn |
| Asn | Gln*, His, Lys, Arg, Asp |
| Asp | Glu*, Asn |
| Cys | Ser |
| Gln | Asn*, His, Lys, |
| Glu | Asp*, γ-carboxyglutamic acid (Gla) |
| Gly | Pro |
| His | Asn, Gln, Lys, Arg* |
| Ile | Leu*, Val, Met, Ala, Phe, norleucine (Nle) |
| Leu | Nle, Ile*, Val, Met, Ala, Phe |
| Lys | Arg*, Gln, Asn, ornithine (Orn) |
| Met | Leu*, Ile, Phe, Nle |
| Phe | Leu*, Val, Ile, Ala |
| Pro | Gly*, hydroxyproline (Hyp), Ser, Thr |
| Ser | Thr |
| Thr | Ser |
| Trp | Tyr |
| Tyr | Trp, Phe*, Thr, Ser |
| Val | Ile, Leu*, Met, Phe, Ala, Nle |

*indicates preferred conservative substitutions

In certain aspects, where an analogue is prepared by synthesis, the analogue may also include an amino acid or amino acids not encoded by the genetic code, such as γ-carboxyglutamic acid and hydroxyproline. For example, D-amino acids rather than L-amino acids may be included. A list of amino acids not encoded by the genetic code is provided in Table 2. In a certain preferred embodiments, the analogue is a mimetic of CSF-1 such as a peptido-mimetic. However, it is not always necessary that an analogue of CSF-1 have amino acid sequence identity and/or similarity. In certain aspects an analogue may not be proteinaceous at all. In certain embodiments an analogue may have at least 75%, such as at least 80%, at least 85%, at least 90%, at least 91%, at least 92%, at least 93%, at least 94%, at least 95%, at least 96%, at least 97%, at least 98% or at least 99% homology with CSF-1.

TABLE 2

List of amino acids not encoded by the genetic code

| | | |
|---|---|---|
| α-aminobutyric acid | D-α-methylhistidine | L-N-methyl-t-butylglycine |
| α-amino-α-methylbutyrate | D-α-methylisoleucine | L-norleucine |
| Aminocyclopropane-carboxylate | D-α-methylleucine | L-norvaline |
| Aminoisobutyric acid | D-α-methyllysine | α-methyl-aminoisobutyrate |
| Aminonorbornyl-carboxylate | D-α-methylmethionine | α-methyl-α-aminobutyrate |
| Cyclohexylalanine | D-α-methylornithine | α-methylcyclohexyl alanine |
| Cyclopentylalanine | D-α-methylphenylalanine | α-methylcylcopentyl alanine |
| L-N-methylisoleucine | D-α-methylproline | α-methyl-α-napthyl alanine |
| D-alanine | D-α-methylserine | α-methylpenicillamine |
| D-arginine | D-α-methylthreonine | N-(4-aminobutyl)glycine |
| D-aspartic acid | D-α-methyltryptophan | N-(2-aminoethyl)glycine |
| D-cysteine | L-N-methylalanine | N-(3-aminopropyl)glycine |
| D-glutamate | L-N-methylarginine | N-amino-α-methyl butyrate |
| D-glutamic acid | L-N-methylasparagine | α-napthylalanine |
| D-histidine | L-N-methylaspartic acid | N-benzylglycine |

TABLE 2-continued

List of amino acids not encoded by the genetic code

| | | |
|---|---|---|
| D-isoleucine | L-N-methylcysteine | N-(2-carbamylediyl)glycine |
| D-leucine | L-N-methylglutamine | N-(carbamylmethyl)glycine |
| D-lysine | L-N-methylglutamic acid | N-(2-carboxyethyl)glycine |
| D-methionine | L-N-methylhistidine | N-(carboxymethyl)glycine |
| D-ornithine | L-N-methylleucine | N-cyclobutylglycine |
| D-phenylalanine | L-N-methyllysine | N-(N-(3,3-diphenylpropyl carbamylmethyl)glycine |
| D-proline | L-N-methylmethionine | N-(N-(2,2-diphenylethyl carbamylmethyl)glycine |
| D-serine | L-N-methylnorleucine | 1-carboxy-1-(2,2-diphenyl-ethylamino)cyclopropane |
| D-threonine | L-N-methylnorvaline | L-α-methyltryptophan |
| D-tryptophan | L-N-methylornithine | N-cycloheptylglycine |
| D-tyrosine | L-N-methylphenylalanine | N-cyclohexylglycine |
| D-valine | L-N-methylproline | N-cyclodecylglycine |
| D-α-methylalanine | L-N-medylserine | L-α-methylnorleucine |
| D-α-methylarginine | L-N-methylthreonine | L-α-methylornithine |
| D-α-methylasparagine | L-N-methyltryptophan | L-α-methylproline |
| D-α-methylaspartate | L-N-methyltyrosine | L-α-methylthreonine |
| D-α-methylcysteine | L-N-methylvaline | L-α-methyltyrosine |
| D-α-methylglutamine | L-N-methylethylglycine | L-N-methylhomo-phenylalanine |
| D-α-methyltyrosine | L-α-methylleucine | L-α-methylserine |
| L-α-methylmethionine | L-α-methyllysine | L-α-methylphenylalanine |
| L-α-methylnorvatine | L-α-methylvaline | |

The term "derivative" is to be understood to refer to any molecule that is derived (substantially derived) or obtained (substantially obtained) from CSF-1, but retains similarity, or substantial similarity, in biological function of CSF-1. In certain aspects, the biological function is the ability to promote organ development. A derivative may, for instance, be provided as a result of cleavage of CSF-1 to produce biologically-active fragments, cyclisation, bioconjugation and/or coupling with one or more additional moieties that improve, for example, solubility, stability or biological half-life, or which act as a label for subsequent detection or the like. A derivative may also result from post-translational or post-synthesis modification such as the attachment of carbohydrate moieties, or chemical reaction(s) resulting in structural modification(s) such as alkylation or acetylation of an amino acid(s) or other changes involving the formation of chemical bonds. In a particularly preferred embodiment of a derivative suitable for use in the present invention, the derivative is the mature domain of CSF-1. In another preferred embodiment of a derivative suitable for use in the methods disclosed herein, the derivative is a biologically active, C-terminal fragment of CSF-1 (e.g. a CSF-1 fragment comprising the C-terminal amino acids 1 to 150 of the 536 amino acid protein). Further embodiments of a derivative of CSF-1 include CSF-1 comprising chemically modified side chains (e.g. pegylation of lysyl e-amino groups), C- and/or N-termini (e.g. acylation of the N-terminal with acetic anhydride), or linked to various carriers (e.g. human serum albumin or histidine ($His_6$) tag).

CSF-1 produced from synthetic protein synthesis and chemical ligation may be used as a source for delivery of large amounts of protein to animals or infants. These synthesized protein analogues may have improved potency or pharmacokinetic properties in comparison to natural CSF-1. CSF-1 protein may be made by first making individual peptide segments of the protein using solid-phase peptide synthesis (SPPS) and then after purification, joining the segments chemically, or via ligation, in solution to form the full-length polypeptide. To facilitate the ligation of individual peptide segments an N-terminal cysteine residue (generally occurring naturally in the protein sequence) and a C-terminal thioester (prepared on-resin) may be needed. After synthesis, the unfolded full-length CSF-1 polypeptide may be folded into its biologically active conformation.

Preferably, certain embodiments disclosed involve the administration of at least one recombinant human CSF-1 (rhCSF-1), in particular, bacterially-expressed, non-glycosylated recombinant human CSF-1.

CSF-1, or a precursor, variant, analogue or derivative thereof, may be administered to the premature infant or foetus by any effective method, some of which are known. For example, for the premature infant, the route of administration can be selected from, for example, intramuscular (i.m.), intravenous (i.v.), topical, such as inhalational administration, intratracheal, subcutaneous (s.c.) administration and/or combinations thereof. On the other hand, for the foetus, the route of administration may be selected from i.m., i.v., s.c, intrauterine (i.u.), oral, inhalational administration to the pregnant mother, and/or combinations thereof.

In some embodiments, rather then systemic administration, it may be desirable for the route of administration to be localized to one or more specific organs or portions of the body, such as by direct application of the therapeutic to the target treatment area or areas. In some embodiments, the composition may be an immediate release dosage form. In other embodiments the composition may be a time release dosage form, including an implantable controlled release form. In some embodiments, the dosage forms may include tablets, dispersions, suspensions, solutions, injections, syrups, troches, capsules suppositories, aerosols, transdermal patches and the like.

Certain embodiments may be administered to ventilated premature infants using aerosol delivery. "Preterm" or "premature" birth can be defined as delivery before approximately the thirty-seventh week of pregnancy. Preterm deliveries can be further delineated as either "very preterm" (before approximately the thirty-third week) or "moderately preterm" (between the approximately thirty-third and approximately the thirty-sixth weeks). Mechanical ventilation that is heated or non-heated; and humidified or non-humidified may be performed in infants. Because of the small tidal volumes and high respiratory rates required for an infant, ventilation may be time or pressure cycled, with a continuous flow of gas circulating through the ventilator circuit.

Certain embodiments of the composition and methods disclosed may be include delivery of CSF-1 with ventilation by aerosol delivery using either a vibrating mesh nebulizer, a jet nebuliser, a metered dose inhaler (MDI), an ultrasonic nebulizer, or an electric pump nebuliser. For example, CSF-1 may be administered in the nebulizer as a bolus dose before the initiation of positive pressure ventilation. In another example CSF-1 may be delivered using continuous feed through an infusion set into a nebulizer. Such a method will allow dosing of aerosol at different rates by adjusting the flow of the drug/unit of time into the nebulizer. Nebulization of certain embodiments disclosed herein may ensure more effective drug delivery to, for example, the lung alveoli of the premature infants.

In certain embodiments, nebulization treatment may be delivered as soon as possible after birth and delivered either intermittently or with continuous aerosol therapy. Continuous nebulization therapy may involve the delivery of prescribed dose of, for example, CSF-1 in diluents or sterile saline or phosphate buffered-saline over 8 hour periods. CSF-1 may be delivered with a small volume-limited or large-volume nebuliser with infusion pump. The volume of CSF-1 to be delivered to infants in the nebulizer may be in the range of 5-15 ml. The CSF-1 may be added to the pediatric nebulizer unit in the inspiratory limb of the ventilator circuit about 10-30 cm away from the patient wye.

The nebulisers may be placed in the ventilator manifold and set to deliver a CSF-1 to an infant at a dose ranging from 0.01-1000 µg/hour of CSF-1 continuously over 8 hours for 1 day, 2 days, 3 days, 4 days, 5 days, 6 days or 7 consecutive days. Typically, such an amount may be, in the case of administration to the premature infant, in the range of about 0.1 to 500 µg/h, about 0.05 to 500 µg/h, about 0.2 to 400 µg/h, 0.1 to 1000 µg/h, about 0.05 to 1000 µg/h, about 0.1 to 1000 µg/h, about 0.5 to 300 µg/h, about 0.75 to 200 µg/h about 1 to 100 µg/h, about 1 to 100 µg/h about 1.25 to 30 µg/h, or about 0.5 to 50 µg/h and, in certain aspects about 0.5 to 200 µg/h, about 0.05 to 100 µg/h, about 0.25 to 150 µg/h, about 0.5 to 50 µg/h, about 1 to 100 µg/h, about 0.75 to 200 µg/h, about 0.5 to 30 µg/h, or about 0.1 to 75 µg/h.

Additionally, in some embodiments, the nebulisers may deliver CSF-1 to infants at a dose ranging from 0.01-1000 mg/hour of CSF-1. CSF-1 to the infants at a dose ranging from 0.01-1000 mg/hour of CSF-1 continuously over 8 hours for 1 day, 2 days, 3 days, 4 days, 5 days, 6 days or 7 consecutive days. Typically, such an amount may be, in the case of administration to the premature infant, in the range of about 0.1 to 500 mg/h, about 0.05 to 500 mg/h, about 0.2 to 400 mg/h, 0.1 to 1000 mg/h, about 0.05 to 1000 mg/h, about 0.1 to 1000 mg/h, about 0.2 to 400 mg/h, about 0.5 to 300 mg/h, about 0.75 to 200 mg/h about 1 to 100 mg/h, about 1 to 100 mg/h about 1.25 to 30 mg/h, or about 0.5 to 50 mg/h and, in certain aspects about 0.5 to 200 mg/h, about 0.05 to 100 mg/h, about 0.25 to 150 mg/h, about 0.5 to 50 mg/h, about 1 to 100 mg/h, about 0.75 to 200 mg/h, about 0.5 to 30 mg/h, or about 0.1 to 75 mg/h.

Alternatively, in some embodiments, CSF-1 and/or a precursor, variant, analogue, derivative thereof or combination thereof, may be administered to a premature infant directly into the bloodstream by intramuscular (i.m.), intravenous (i.v.), subcutaneous (s.c.) administration and/or combinations thereof. The most familiar type of vascular access is a peripheral intravenous line (PIV) attached to an i.v. pump. In newborns, PIVs often may be placed in veins of the hand, foot, or scalp that may enable delivery of CSF-1 in combination with fluids, nutrients or other pharmaceutical agents. The PIV may enable the continuous infusion or pulse infusion of CSF-1 for hours to days. CSF-1 may be delivered by i.v infusion to the infants at a dose ranging from 0.01-1000 µg/hour of CSF-1 continuously over 8 hours for 1 day, 2 days, 3 days, 4 days, 5 days, 6 days or 7 consecutive days. Typically, such an amount may be, in the case of administration to the premature infant, in the range of about 0.1 to 500 µg/h, about 0.05 to 500 µg/h, about 0.2 to 400 µg/h, 0.1 to 1000 µg/h, about 0.05 to 1000 µg/h, about 0.1 to 1000 µg/h, about 0.5 to 300 µg/h, about 0.75 to 200 µg/h about 1 to 100 µg/h, about 1 to 100 µg/h about 1.25 to 30 µg/h, or about 0.5 to 50 µg/h and, in certain aspects about 0.5 to 200 µg/h, about 0.05 to 100 µg/h, about 0.25 to 150 µg/h, about 0.5 to 50 µg/h, about 1 to 100 µg/h, about 0.75 to 200 µg/h, about 0.5 to 30 µg/h, or about 0.1 to 75 µg/h.

CSF-1 may be delivered to infants by i.v infusion at a dose ranging from 0.01-1000 mg/hour of CSF-1 at a dose ranging from 0.01-1000 mg/hour of CSF-1 continuously over 8 hours for 1 day, 2 days, 3 days, 4 days, 5 days, 6 days or 7 consecutive days. CSF-1 may be delivered in the range of about 0.1 to 500 mg/h, about 0.05 to 500 mg/h, about 0.2 to 400 mg/h, 0.1 to 1000 mg/h, about 0.05 to 1000 mg/h, about 0.1 to 1000 mg/h, about 0.2 to 400 mg/h, about 0.5 to 300 mg/h, about 0.75 to 200 mg/h about 1 to 100 mg/h, about 1 to 100 mg/h about 1.25 to 30 mg/h, or about 0.5 to 50 mg/h and, in certain aspects about 0.5 to 200 mg/h, about 0.05 to 100 mg/h, about 0.25 to 150 mg/h, about 0.5 to 50 mg/h, about 1 to 100 mg/h, about 0.75 to 200 mg/h, about 0.5 to 30 mg/h, or about 0.1 to 75 mg/h.

In some embodiments, the CSF-1, at least one precursor, at least one variant, at least one analogue, at least one derivative, or combinations thereof, may be administered in the form of a composition comprising a carrier (e.g. a pharmaceutically acceptable vehicle or diluent such as saline). Infants that are intubated may receive CSF-1 as an aerosol with nebulizer treatment before or in combination with another pharmaceutical agent including but not limited to surfactants such as artificial or natural surfactants, such as EXOSURF, PUMACTANT, KL-4, VENTICUTE. ALVEOFACT, CUROSURF, INFASURF or SURVANTA, anti-inflammatory agents or corticosteroids, fluids for hydration, heparin, albuterol, antibiotics, ibruprofen, nutritional supplements, vitamin supplements, mineral supplements, sildenafil, other colony stimulating factors such as G-CSF or GM-CSF, and/or IGF-I, IGF-II, HGF, EGF, or mixtures thereof.

In some embodiments, CSF-1 may be delivered to the foetus via the pregnant woman by i.v bolus injection typically at a concentration range of 0.1-1 g/kg body weight. The exact amount may vary depending upon a variety of factors including the relative activity, metabolic stability and length of action of the CSF-1, precursor, variant, analogue or derivative thereof, the route and time of administration, the degree, or likely degree, of organ underdevelopment, and, in the case of the foetus, the general health of the pregnant mother.

Alternatively, in some embodiments, CSF-1 may be delivered by aerosol nebulisation with or without ventilation. CSF-1 may be administered in the nebulizer as a bolus dose before the initiation of positive pressure ventilation. Alternatively, CSF-1 may be delivered by continuous feed through an infusion set into a nebulizer. The doses and timing for CSF-1 delivery may be similar to infants described above.

In some embodiments, in pregnant warm blooded animals, such as mares, pigs, catties, dogs and other livestock, CSF-1 may be delivered to the foetus by bolus injection into the bloodstream of the mother using intramuscular, intravenous, or subcutaneous administration or combinations of the above at a concentration range typically from 0.1-1 g/kg of body weight. Alternatively, in other embodiments, CSF-1 may be delivered to such animals or to infant animals by aerosol nebulisation with or without ventilation by administration of a bolus in the nebuliser before initiation of positive pressure or by using a continuous feed through an infusion set into a nebuliser. The doses and timing for CSF-1 delivery may be similar to human infants described above.

In some embodiments, the CSF-1, at least one precursor, at least one variant, at least one analogue, at least one derivative, or combinations thereof, may be administered in the form of a composition comprising a carrier (e.g. a pharmaceutically acceptable excipient, vehicle or diluent). Such compositions may further comprise other therapeutic agents (e.g. IGF-I, IGF-II, HGF, EGF, or mixtures thereof) and may be formulated by, for example, employing conventional solid or liquid excipients, vehicles, diluents or combinations thereof, as well as pharmaceutical additives of a type appropriate to the mode of desired administration (for example, excipients, binders, preservatives, stabilisers, flavours, colorants, buffers etc.). Non-limiting examples of suitable excipients, vehicles and diluents may be found in Gennaro, Alfonso, Remington's Pharmaceutical Sciences, 18$^{th}$ edition. Mack Publishing Co. (1990), in Gennaro, Alfonso, Remington: The Science and Practice of Pharmacy, 19$^{th}$ edition (1995) and, 20$^{th}$ edition (2003) and/or in University of the Sciences in Philadelphia (editor) Remington: The Science and Practice of Pharmacy and 21$^{St}$ edition (2005), the entire contents of each of which is hereby incorporated by reference. Examples of some excipients include sterile liquids, such as water and oils, including those of petroleum, animal, vegetable or synthetic origin, such as peanut oil, soybean oil, mineral oil, sesame oil, saline solutions, aqueous dextrose solutions, aqueous glycerol solutions, buffers, proteins such as serum albumin, amino acids such as aspartic acid, glutamic acid, lysine, arginine, glycine, histidine, peptides, carbohydrates such as saccharides, polymeric additives, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents, or combinations thereof. Examples of some buffers that may be used include salts prepared from an inorganic acid such as mineral acid salts, such as hydrochlorides, bromides, and sulfates and salts prepared from an organic acid or base, such as salts of citric acid, propionic acid, malonic acid, ascorbic acid, gluconic acid, carbonic acid, tartaric acid, succinic acid, acetic acid, or phthalic acid or Tris, tromethamine hydrochloride, phosphate buffers, or combinations thereof.

The CSF-1, at least one precursor, at least one variant, at least one analogue, at least one derivative, or combinations thereof, may be administered in any amount that is effective in treating complications arising from low birth weight in mammals, such as humans, pigs, horses, dogs or other livestock, such as in premature infants or foetuses, in promoting organ development in the premature infant or foetus and/or in promoting bone growth and/or enhancing bone development and/or maturation in mammals, such as humans, pigs, horses, dogs or other livestock, such as in premature infants or foetuses. Typically, such an amount will be, in the case of administration to the premature infant, in the range of about 0.1 to 500 µg/kg/day, about 0.05 to 500 µg/kg/day, about 0.1 to 500 µg/kg/day, about 0.2 to 400 µg/kg/day, about 0.5 to 300 µg/kg/day, about 0.75 to 200 µg/kg/day about 1 to 100 µg/kg/day, about 1 to 100 µg/kg/day about 1.25 to 30 µg/kg/day, or about 0.5 to 50 µg/kg/day and, in certain aspects more preferably, about 0.5 to 200 µg/kg/day, about 0.05 to 100 µg/kg/day, about 0.25 to 150 µg/kg/day, about 0.5 to 50 µg/kg/day, about 1 to 100 µg/kg/day, about 0.75 to 200 µg/kg/day, about 0.5 to 30 µg/kg/day, or about 0.1 to 75 µg/kg/day and for the foetus (where administration is via the pregnant mother). However, the exact amount may substantially vary depending upon a variety of factors including, but not limited to, the relative activity, metabolic stability and length of action of the CSF-1, at least one precursor, at least one variant, at least one analogue, at least one derivative, or combinations thereof, the route and time of administration, the degree, or likely degree, of organ underdevelopment, the type and severity of complications arising from the low birth weight, the age of the foetus or premature infant and, in the case of the foetus, the general health of the pregnant mother.

Administration of the CSF-1, at least one precursor, at least one variant, at least one analogue, at least one derivative, or combinations thereof, to the premature infant may commence upon birth and continue until a desired level of organ development is observed. Thus, for the lung, a desired level of lung development may be achieved when the saccular phase has been completed and/or the infant no longer requires a mechanical ventilator. For the kidney, a desired level or organ development may be achieved when renal function has been improved and/or the numbers of nephrons has been increased since birth. For the foetus, administration of the CSF-1, at least one precursor, at least one variant, at least one analogue, at least one derivative thereof, or combinations thereof, may commence from about gestational week 4, about gestational week 5, about gestational week 7, about gestational week 10, about gestational week 12, about gestational week 14, or about gestational week 19, but in certain aspects preferably, commences after about week 20, about week 22, about week 24, or about week 26.

Certain embodiments disclosed also encompasses the administration of at least one nucleic acid molecule encoding CSF-1, at least one precursor, at least one variant, at least one analogue, at least one derivative thereof, or combinations thereof, such that the CSF-1, at least one precursor, at least one variant, at least one analogue, at least one derivative thereof, or combinations thereof, are expressed from the nucleic acid molecule by the premature infant or foetus (and/or pregnant mother).

In certain embodiments, suitable nucleic acid molecules may be single or double stranded, such as mRNA, ssRNA, dsRNA, ssDNA and dsDNA. However, in certain preferred aspects, the nucleic acid molecule will be dsDNA.

The nucleic acid molecule may be incorporated into an expression construct or vector in accordance with any effective method, some of which are known. Typically, in certain aspects the nucleic acid molecule will be introduced into such an expression construct or vector such that transcription of the nucleic acid molecule is driven by a promoter sequence provided by the expression construct or vector. In certain aspects it is preferred that the expression construct or vector is adapted for expression in mammalian cells, tissues or organs such as lung and/or kidney cells.

In certain aspects it is preferred that the nucleic acid molecule is incorporated into at least one viral vector such as an adenovirus, lentivirus or poxvirus vector.

The nucleic acid molecule may be administered to the premature infant or foetus (via the pregnant mother) by any effective method, some of which are well know (e.g. liposome-mediated transfection, or for viral vectors, viral transformation).

Administration of the at least one nucleic acid molecule encoding the CSF-1, at least one precursor, at least one variant, at least one analogue, at least one derivative thereof, or combinations thereof, to the premature infant may occur upon birth, whereas for the foetus, administration of the at least one nucleic acid molecule encoding the CSF-1, at least one precursor, at least one variant, at least one analogue, at least one derivative thereof, or combinations thereof, may occur from about gestational week 4, about gestational week 5, about gestational week 7, about gestational week 10, about gestational week 12, about gestational week 14, or about gestational week 19, but in certain aspects preferably, commences after about week 20, about week 22, about week 24, or about week 26.

Certain methods disclosed are particularly suitable for increasing growth and/or enhancing lung maturation and nephrogenesis in the kidney.

In certain aspects disclosed, the methods of promoting growth and/or enhanced lung development and/or maturation in a premature infant or foetus, comprise the step of administering to the infant or foetus;

at least one colony stimulating factor-1 protein (CSF-1), or at least one precursor, at least one variant, at least one analogue, at least one derivative thereof, or combinations thereof, or at least one nucleic acid molecule encoding said colony stimulating factor-1 protein (CSF-1), at least one precursor, at least one variant, at least one analogue, at least one derivative thereof, or combinations thereof.

In certain aspects disclosed, the methods of promoting growth and/or enhanced lung development and/or maturation in a premature infant or foetus, comprise the step of administering to the infant or foetus;

colony stimulating factor-1 protein (CSF-1), or precursor, variant, analogue, or derivative thereof or nucleic acid molecule encoding said colony stimulating factor-1 protein (CSF-1), precursor, variant, analogue, or derivative thereof.

And, in certain aspects disclosed a method of promoting growth, maturation and/or enhanced kidney development in a premature infant or foetus is provided, said method comprising the step of administering to the infant or foetus;

colony stimulating factor-1 protein (CSF-1), or a precursor, variant, analogue or derivative thereof, or a nucleic acid molecule encoding said colony stimulating factor-1 protein (CSF-1), or a precursor, variant, analogue or derivative thereof.

In certain aspects disclosed, methods are provided for promoting growth, maturation and/or enhanced kidney development in a premature infant or foetus, comprising the step of administering to the infant or foetus;

at least one colony stimulating factor-1 protein (CSF-1), at least one precursor, at least one variant, at least one analogue, at least one derivative thereof or combinations thereof, or at least one nucleic acid molecule encoding said colony stimulating factor-1 protein (CSF-1), at least one precursor, at least one variant, at least one analogue, at least one derivative thereof, or combinations thereof.

It is anticipated that the certain methods disclosed may be equally applicable to newborn non-human animals and non-human foetuses. In particular, it is anticipated that the methods of the invention might be used in relation to warm blooded animal, for example. But not limited to, thoroughbred horses, stud animals and companion animals such as dogs and cats.

In order that the nature of the present inventions may be more clearly understood, preferred forms thereof will now be described with reference to the following non-limiting examples.

In some embodiments, the methods of treating complications arising from low birth weight in mammals, such as humans, pigs, horses, dogs or other livestock, such as in premature infants or foetuses, in promoting organ development in the premature infant or foetus and/or in promoting bone growth and/or enhancing bone development and/or maturation in mammals, such as humans, pigs, horses, dogs or other livestock, such as in premature infants or foetuses may include co-treatment with other therapeutic modalities.

For example, in some embodiments, prior to birth the methods may include treatment of the mother by administering to the mother at least one colony stimulating factor-1 protein (CSF-1), at least one precursor, at least one variant, at least one analogue, at least one derivative thereof or combinations thereof, or at least one nucleic acid molecule encoding said colony stimulating factor-1 protein (CSF-1), at least one precursor, at least one variant, at least one analogue, at least one derivative thereof, or combinations thereof;

in combination with treatment with one or more drugs or other substances to treat an underlying cause of low birth weight or complications resulting from low birth weight, such as drugs for hypertension, infections or diabetes, coticosteroids, tocolytics, nutritional supplements, vitamin supplements, mineral supplements, albuterol, antibiotics, heparin, other colony stimulating factors such as G-CSF or GM-CSF, surfactants such as artificial or natural surfactants, such as EXOSURF, PUMACTANT, KL-4, VENTICUTE. ALVEOFACT, CUROSURF, INFASURF or SURVANTA, IGF-I, IGF-II, HGF, EGF, sildenafil, ibuprofen or in combination with surgical treatment of the mother and/or fetus.

In some embodiments, prior to birth the treatment of the mother may include treatment in a dosage form that enhances transplacental drug delivery, such as using a liposomal form of the administered treatment. Such liposomal forms may be created having a variety of sizes, charges and lipid compositions. In some embodiments, such liposomal forms may be anionic small unilamellar liposomes.

In some embodiments after birth, the methods herein may include administering to the premature or low birth weight infant at least one colony stimulating factor-1 protein (CSF-1), at least one precursor, at least one variant, at least one analogue, at least one derivative thereof or combinations thereof, or at least one nucleic acid molecule encoding said colony stimulating factor-1 protein (CSF-1), at least one precursor, at least one variant, at least one analogue, at least one derivative thereof, or combinations thereof;

in combination with treatment with one or more drugs or other substances to treat an underlying cause or complication of low birth weight, such as coadministration of surfactant therapy, such as administration of surfactant, such as artificial or natural surfactants, such as EXOSURF, PUMACTANT, KL-4, VENTICUTE. ALVEOFACT, CUROSURF, INFASURF or SURVANTA, albuterol, heparin, sildenafil, ibuprofen, nutritional supplementation, vitamin and/or mineral supplementation, surgery, IGF-I, IGF-II, HGF, EGF, antibiotic therapy, other colony stimulating factors such as G-CSF or GM-CSF, other drug therapy to treat any complications of low birth weight.

In some embodiments, the CSF-1 may be provided as a kit, such as at least one colony stimulating factor-1 protein (CSF-1), at least one precursor, at least one variant, at least one analogue, at least one derivative thereof or combinations thereof, or at least one nucleic acid molecule encoding said colony stimulating factor-1 protein (CSF-1), at least one precursor, at least one variant, at least one analogue, at least one derivative thereof, or combinations thereof in conjunction with instructions for administration, including dosing instructions, adverse event information and adverse interaction information, other dosing equipment or coadministration therapy-related drugs, equipment and/or instructions.

For example, in some embodiments of the kits, at least one colony stimulating factor-1 protein (CSF-1), at least one precursor, at least one variant, at least one analogue, at least one derivative thereof or combinations thereof, may be provided as an ampule that may be added to a nebulisation unit or as a pre-dosed nebulisation system that attaches to a ventilator system for premature babies. In some embodiments of the kits, at least one colony stimulating factor-1 protein (CSF-1), at least one precursor, at least one variant, at least one analogue, at least one derivative thereof or combinations thereof, may be provided in pre-dosed syringes, with infant-specific i.v. lines and infant-sized needles or other administration devices. In some embodiments, CSF-1 kits may be provided as a mixture of at least one colony stimulating factor-1 protein (CSF-1), at least one precursor, at least one variant, at least one analogue, at least one derivative thereof or combinations thereof with saline, buffered saline or other diluent and/or as a mixture with other colony stimulating factors, such as G-CSF and/or GM-CSF, drugs such as albuterol, antibiotics, or IGF-I, IGF-II, HGF, EGF, or a surfactant or mixtures thereof.

EXAMPLES

Example 1

Characterizing the Location and Arrival of Resident Renal Macrophages
Materials and Methods
CSF-1
All experiments described herein used human recombinant CSF-1.
Isolation of Renal Embryonic Tissue and Macrophages
Outbred CD1 female mice were mated and sacrificed by cervical dislocation for the collection of control kidney tissue at E15.5. Embryonic kidneys were dissected in ice-cold PBS and stored at −70° C. in preparation for RNA extraction.
Male c-fms transgenic mice (Sasmono, et al., 2003, supra) were mated to CD1 outbred females. Pregnant females were sacrificed at E15.5 and transgenic offspring were determined by visualization of c-fms EGFP expression in the placenta of the embryos. The kidneys of both transgenic and non-transgenic embryos were dissected separately in ice-cold PBS. 10-20 kidneys were incubated in 1 ml Dissociation Media (1 mg/ml Collagenase B. 1.2 U/ml Dispase, 5 U/ml DNase II, in HANKS media) at 37° C. for 20 min. Kidneys were then dissociated with a P-1000 and incubated for a further 5 min at 37° C. This step was repeated before the kidneys were dissociated with a 23-gauge syringe and passed through a 40 uM cell strainer (BD Bioscience). An equal volume of ice-cold PBS was washed through the strainer and the cells were centrifuged at 3000×rpm for 5 min. The supernatant was discarded and the cells resuspended in 2-3 ml of ice-cold PBS. The cells were passed again through a 40 uM cell strainer, checked under a microscope to ensure they were a single-cell suspension, and stored on ice ready for fluorescence activated cell sorting (FACS). Isolation of EGFP positive macrophages was carried out on a FACS Vantage SE DiVa flow cytometer (BD Biosciences). Approximately 200 transgenic kidneys were subjected to FACS analysis with non-transgenic littermate kidneys used as a reference. All animal experimentation was covered by Animal Ethics Committee number IMB/479/03/NIH.

RNA In Situ Hybridisation
Section RNA in situ hybridisation was performed as previously described (Roche DIG Application Manual) with minor modifications (Holmes G P, et al., Mech. Dev., 79:57-72, 1998). Sections were dehydrated through an ethanol series prior to hybridization overnight at 65° C. Posthybridisation washes consisted of 6×SSC (5 min, 65° C.), 2×SSC/50% formamide/10 mM EDTA (30 min, 65° C.), 2×SSC (2×30 min, 65° C.) and 0.2×SSC (2×30 min, 65° C.).
Isolation and Preparation of Tissue for Confocal Analysis
Male c-fms transgenic mice (Sasmono, et al., 2003, supra) were mated to CD1 outbred females. Pregnant females were sacrificed at E11.5, E12.5, E15 and newborn and transgenic offspring were determined by visualization of c-fms EGFP expression in the placenta of the embryos. The kidneys of transgenic embryos were dissected separately in ice-cold PBS. c-fms kidneys were fixed in 4% paraformaldehyde for 3 hrs at room temperature. The kidneys were subsequently equilibrated in 30% sucrose overnight at 4° C. before being mounted in Tissue-Tek OCT medium in isopentane cooled over dry ice.
Results
To facilitate the isolation and characterisation of tissue macrophages, we have generated transgenic mice in which the control elements of the c-fms gene direct expression of a green fluorescent protein (EGFP) reporter. In the so-called MacGreen mice, all tissue macrophages, including interstitial macrophages in the kidney and phagocytes in the embryo from the earliest appearance in the yolk sac, express high levels of EGFP fluorescence (Sasmono, et al., 2003, supra).
As shown in FIG. 1 (left), GFP+ cells isolated from embryonic day 15.5 kidneys of c-fms-EGFP transgenic mice represented 2.8% of total cells.
Confocal analysis of kidneys from these mice revealed that these cells appear within the kidney from 12 days post coitum (dpc) and are spread throughout the renal interstitium. As the tubules of the developing nephrons arise and the interstitial space contracts, the renal macrophages become intimately associated with the basement membranes of the adjacent proximal and distal tubules. Their cellular processes wrap around adjacent tubules (FIG. 1, right) facilitating an intimate relationship with the cells of these tubules.

Example 2

Human Recombinant CSF-1 has a Growth-Promoting Effect on the Developing Kidney. Materials and Methods
Metanephric Organ Culture
Metanephric organ culture was used to test the effect of recombinant CSF-1 on the developing metanephros. Metanephroi from E11.5 mice were grown for 1-6 days on Poretics 13 mm polycarbonate inserts (Osmonics Inc) with a membrane pore size of 1.0 µm at 37° C. with 5% CO2 in 300 µl of DMEM/Hams F12 media (Invitrogen) supplemented with 50 µg/ml transferrin and 20 mM glutamine. Metanephroi were either grown in media alone or media supplemented with CSF1 to a final concentration of 100 U/µL (1.25 ng/µL).
Immunofluorescence
Co-immunofluorescence for calbindin-D28K and WT1 was performed at the end of the culture period to visualise growth and differentiation of the ureteric epithelium and formation of early nephron structures in explanted metanephroi as previously described (Piper, et al., 2002, Int. J. Dev. Biol., 46, 545). Metanephroi were fixed in 100% methanol at −20° C. for 20 minutes. Monoclonal anticalbindin-D28K (Sigma Chemical Company) was used at a dilution of 1:100 and C-terminal WT1 polyclonal antibody C19 (Santa Cruz, SC-192) was used at a dilution of 1:100. Secondary antibodies used were Cy3-conjugated anti-rabbit IgG (Sigma) at a dilution of 1:500, and Alexa Fluor 488 conjugated goat anti-mouse (Molecular Probes) at a dilution of 1:200. Explants were also treated with DAPI for visualisation of individual nuclei. Digital images were captured using a Dage "MTI" peltier cooled charge coupled device digital camera attached to an AX70 Olympus microscope, and artificially coloured and overlayed using Adobe Photoshop 7 software.

Statistical Analysis

To semi-quantitatively assess the effects of CSF-1 conditioned media on in vitro metanephric development, branch tips, branch points and WT1-positive bodies (forming nephrons) present in each explanted metanephros were counted. A one-way ANOVA followed by a Tukey's post-hoc test was used to determine if there was a significant difference in the number of ureteric tip, branch and/or WT1 positive bodies in CSF-1-treated metanephroi in comparison to untreated metanephroi.

Results

At 11.5 dpc, mouse embryonic kidneys (metanephroi) are comprised of a T-shaped UB surrounded by MM. These can be isolated via microdissection and cultured as explants for up to 6 days. During culture, the ureteric epithelium undergoes branching morphogenesis and a mesenchyme-to-epithelial transition occurs, generating immature nephrons. Metanephric explant culture is an excellent model system for examining kidney development.

We have established kidney explant culture to screen secreted factors for their ability to perturb or promote kidney development. One of the proteins that we have added to explant cultures is human recombinant CSF-1. The C-terminal 150 amino acids of this protein is bioactive and contains 4 helix bundles similar to those of other members of this cytokine family (G-CSF, GM-CSF). It can be produced in bacteria and correctly fold to form a bioactive protein.

Figure 2:
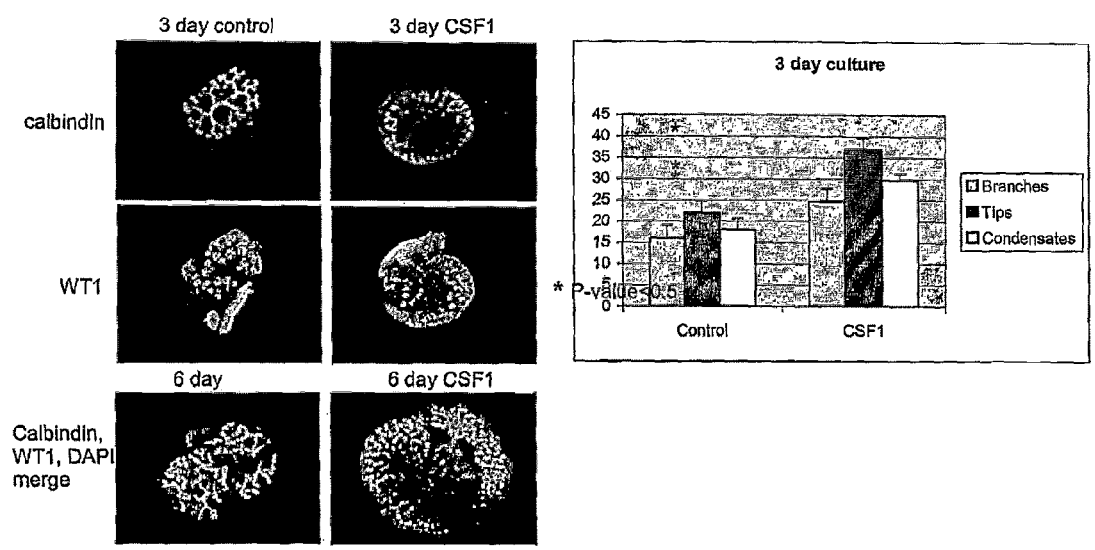
FIG. 2. Metanephric explants cultured with 100U/μL (1.25 ng/μL) human recombinant CSF-1 for 3 days compared to control explants Immunofluorescence was performed to reveal the ureteric tree (calbindin 28KD) and the forming nephrons (WT1). 6 day cultures with WT1, calbindin and DAPI (nuclei) merged show the overall increase in size.

Addition of recombinant CSF1 to kidney explants resulted in a dramatic and statistically significant enhancement of renal development (FIG. 2). Explants grew with the same morphology as normal, but at a much greater rate and to a greater overall size. This was evident after only 24 hours and detectable at doses as low as 100 U/μL. This implies that renal CSF1 signalling via c-fms (CSFR1) on resident macrophages plays a positive role in kidney development.

Example 3

Human Recombinant CSF-1 has a Growth-Promoting Effect on the Damaged Adult Kidney Materials and Methods Mouse Surgery Male c-fms transgenic mice (20-25 g, Monash University Animal House, Australia), carrying a green fluorescent protein (GFP) driven by the c-fms (CSF-1 R) promoter, were divided into 3 groups. The first group (n=4) were anaesthetized with 2% inhaled isofluorane (Abbott Australasia Pty Ltd, Kurnell, Australia) and ischemia/reperfusion (IR) injury was induced via 50 minutes of left renal artery clamping. A vascular clamp (0.4-1.0 mm; S&T Fine Science Tools, CA) was used for this procedure via a flank incision. Each mouse in this group received three intraperitoneal injections of CSF-1 (20 μg/timepoint) at day 3, 4, and 5 after initiation of IR injury. The right contralateral kidney served as a control for CSF-1 treatment.

The second group of mice (n=4) underwent 50 minutes of left renal artery clamping and vehicle injections (phosphate buffered saline; PBS) were administered at days 3, 4, and 5. The third group (n=5) of mice served as a sham-operated control group where the animals were anaesthetized and a flank incision was performed without renal artery clamping. All experiments were approved by a Monash University Animal Ethics Committee which adheres to the "Australian Code of Practice for the Care and Use of Animals for Scientific Purposes".

Preparation of Tissue for Microscopy

At 1 week after IR injury, mice were perfusion-fixed with 4% paraformaldehyde (PFA) under 2% inhaled isofluorane anesthesia. A midline incision was made to expose both the heart and the inferior vena cava. A 27" gauge needle was injected into the left ventricle of mice and flushed for 3 minutes with PBS containing heparin and NaNitropruside. At the same time, the inferior vena cava was cut to provide an outlet for the perfusate. Mice were perfusion-fixed with preheated 4% PFA at 100 mmHg for 10 minutes. Mid-coronal kidney sections were immersion fixed in 4% PFA (Sigma-Aldrich), embedded in paraffin wax and cut at 4 μm. Sections were stained with haematoxylin and eosin and Periodic Acid Schiff (PAS) for histopathological analysis.

For fluorescence visualization of c-fms-EGFP-macrophages, following perfusion-fixation kidney tissue was fixed in 4% PFA for 8 hours, transferred to PBS containing 30% sucrose for overnight incubation at 4° C., embedded in O.C.T. (TissueTek® Japan) and stored at −80° C. Frozen sections were cut (5 μm) using a cryostat (Leica, Germany) and visualized under an Olympus Provis AX70 fluorescent microscope.

For determination of collagen type IV localisation, sections were incubated with 1% bovine serum albumin (BSA). A goat anti-human collagen type IV primary antibody (Southern Biotech, Birmingham, Ala.; 1:100 dilution) was added for 1 hour followed by a chicken anti-goat Alexa Fluor 647 conjugate (1:1000; Molecular Probes). Sections were mounted with Fluorescent Mounting Media (DakoCytomation) before visualization under an Olympus Provis AX70 fluorescent microscope.

Measurement of Proteinuria and Urine Creatinine

Mice were housed in metabolic cages, with free access to food and water on the days of urine collection. Albumin and creatinine levels, and the albumin/creatinine ratio were measured in 24 hour urine samples using an Albuwell murine microalbuminuria ELISA assay and creatinine companion kit (both from Exocell Inc.), respectively.

Results

Promotion of Renal Repair in IR Kidneys with CSF-1 Treatment

Figure 3:
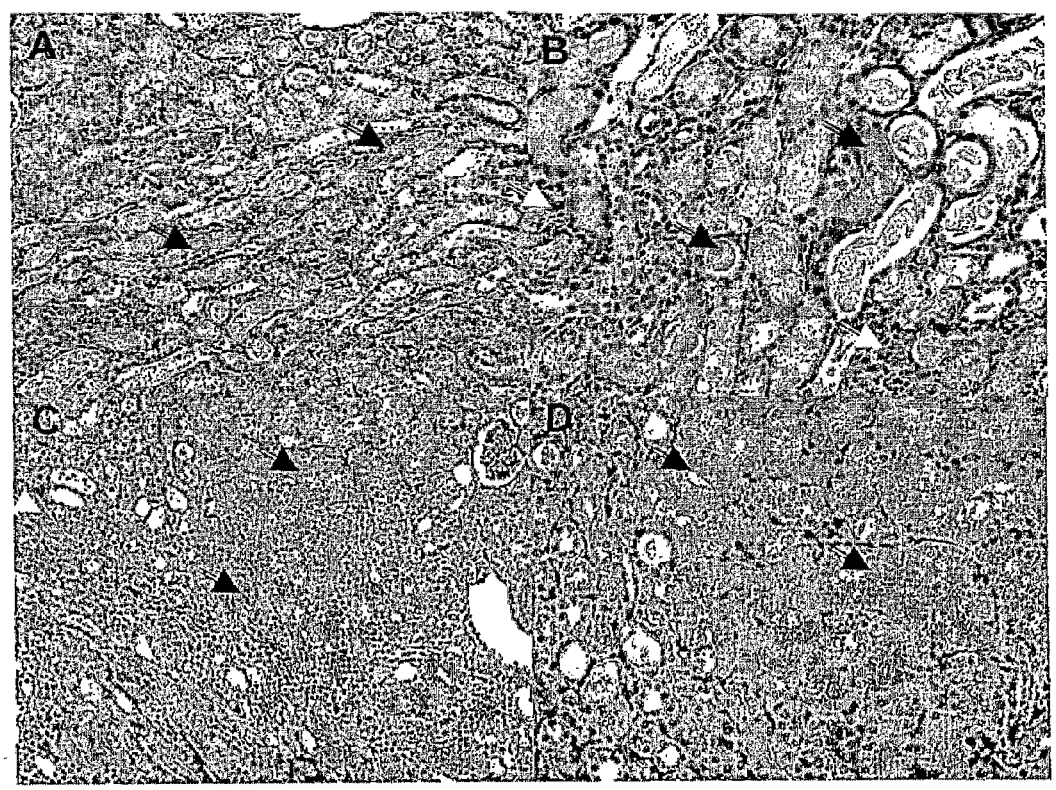
FIG. 3. Representative micrographs demonstrating the histology of mice following 50 minutes of IR injury at 1 week after injury (Panel A and B) compared to mice with IR injury following delayed administered CSF-1 at the same time point (Panel C and D). Numerous tubular casts (black arrows) were evident in the renal medulla by 1 week after IR injury (Mag ×200) (A). At higher power (Mag ×400) interstitial matrix expansion is shown with a prominent inflammatory cell infiltrate (white arrows; B). In IR mice following CSF-1 administration starting at 3 days post-renal artery clamping the majority of the tubular epithelium showed normal histology (black arrows) with very few tubular casts present at 1 week white arrows; C Mag ×200). At higher power (D; Mag ×400) there was widespread tubular epithelial cell replacement (black arrows) with attenuated interstitial matrix expansion.

At 1 week widespread damage was evident in IR kidneys of mice receiving vehicle treatment. Characteristic of the renal damage was extensive loss of tubular epithelium and tubular cast formation particularly in the outer medullary region where numerous tubular casts were observed (FIGS. 3A & B). In these IR kidneys, interstitial matrix expansion was associated with the accumulation of extracellular matrix proteins resulting in the development of interstitial fibrosis (FIGS. 3 A & B). 50 minutes of IR injury led to a severe inflammatory response and the extensive loss of the tubular epithelium, without the necrotic insult demonstrated with longer durations of renal artery clamping.

In comparison, mice with IR injury receiving CSF-1 treatment starting at 3 days after initiation of injury, showed normal renal histology in the cortical and medullary regions (FIG. 3C). In the outer medullary region the tubules appeared intact with complete re-epithelialisation evident (FIG. 3D). There were very few tubular casts apparent in these kidneys (FIGS. 3 C & D). Furthermore, in IR kidneys with CSF-1 treatment there was a marked attenuation of interstitial matrix expansion as a result of diminished interstitial fibrosis.

Functional Recovery of IR Mice with CSF-1 Treatment

Figure 4:
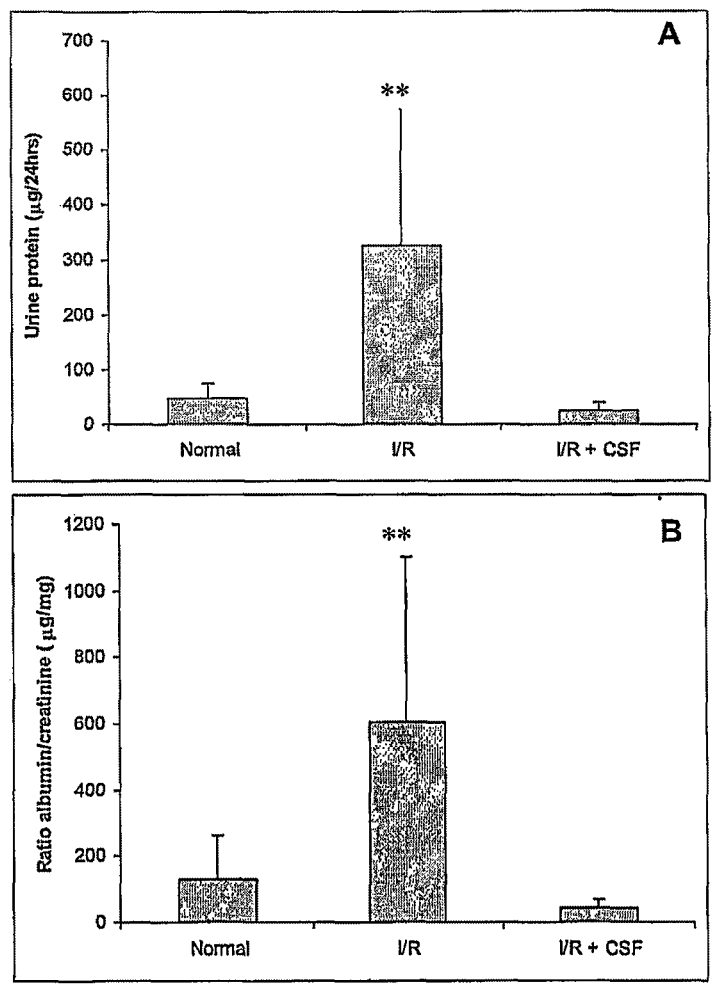
FIG. 4. Measurement of urinary albumin levels (A) and the albumin/creatinine ratio (B) in IR mice with or without the administration of CSF-1 delivered day 3-5 after initiation of injury. The administration of CSF-1 to IR mice was found to reduce urinary protein levels and the albumin/creatinine ratio comparable to control animals. **$P<0.03$; Data are means±SD.

Urine protein levels were measured in 24 hour urine samples obtained from sham-operated control mice and IR mice with/without CSF-1 delayed administration (FIG. 4). There was a significant reduction in the urine protein levels in IR kidneys with CSF-1 treatment compared to IR kidneys without CSF-1 administration (324.4+250.1 vs. 23.84+15.7; P<0.03). Although creatinine was not found to be significantly different between the mice with IR injury compared to control or IR+CSF-1 treatment, the albumin/creatinine ratio was found to be significantly reduced following CSF-1 treatment (42.24±25.60 vs. 604.22+496.20; P<0.03). The fact that urinary creatinine levels were not significantly different between groups is probably reflective of right kidney compensation following the left unilateral renal artery clamping. However, the albumin/creatinine ratio is a good indicator of kidney function.

Figure 5:
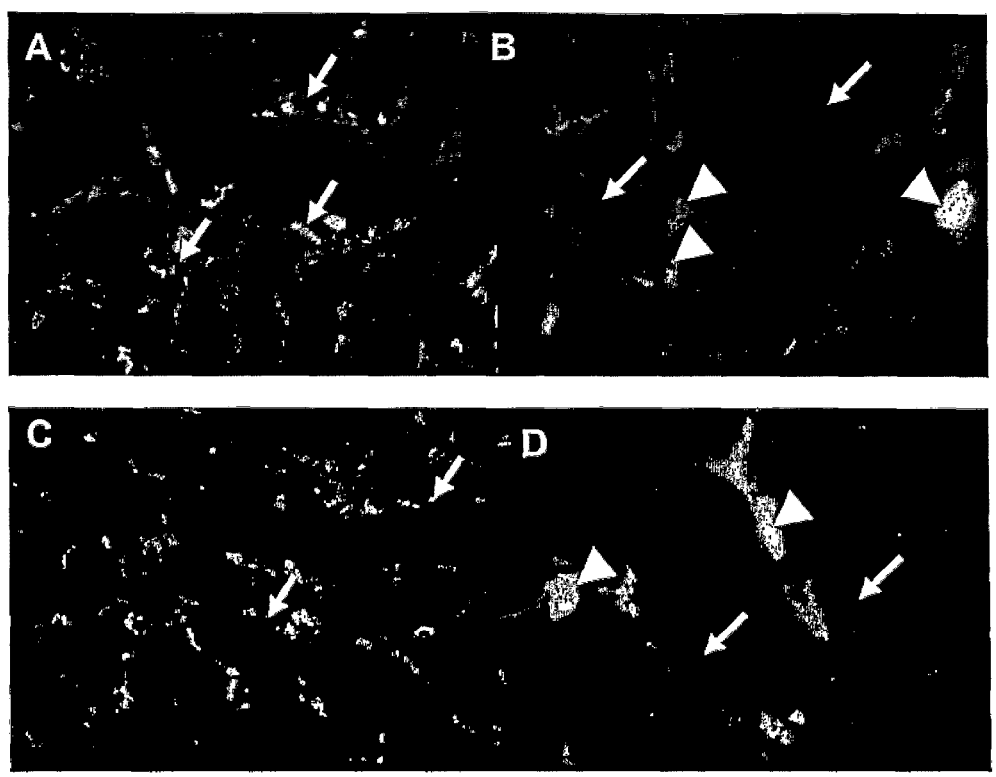
FIG. 5: Immunofluorescence microscopy of type IV collagen in c-fms-GFV mice following IR receiving vehicle (A and B) or CSF-1 treatment (C and D). Panel A demonstrates increased numbers of GFP-positive macrophages in the renal interstitium that was associated with collagen type IV accumulation leading to interstitial expansion (arrows; Mag ×400). At higher power (B; Mag ×1,000) arrows show tubular cast formation (white arrows) in the majority of proximal tubules as a result of loss of epithelial cell integrity. Interstitial macrophages (large arrowheads) can be seen associated with type IV collagen accumulation in IR kidneys. Following CSF-1 treatment, IR kidneys displayed decreased numbers of interstitial GFP-macrophages, and a normal tubulointerstitium that contained a fine framework of collagen type IV (arrows; C; Mag ×400) comparable to normal kidneys. At higher power (D; Mag ×1,000) the CSF-1 treated IR kidneys showed normal architecture with an intact proximal tubular epithelial cell lining (arrows) that was surrounded by few GFP-macrophages in the interstitium (large arrowheads) without evidence of fibrosis.

CSF-1 Reduces Type IV Collagen Accumulation and the Number of Interstitial Macrophages in the IR Kidney In c-fms-GEF IR mice, increased numbers of GFP-positive macrophages in the renal interstitium were associated with collagen type IV accumulation and interstitial expansion (FIGS. 5A & B). Tubular cast formation in the majority of proximal tubules was observed (FIG. 5B) as a result of loss of epithelial cell integrity. Following CSF-1 treatment, IR mouse kidneys displayed decreased numbers of interstitial GFP-macrophages, and a normal tubulointerstitium that contained a fine framework of collagen type IV comparable to normal kidneys (FIGS. 5C & D). Furthermore, the CSF-1 treated IR kidneys showed normal architecture with an intact proximal tubular epithelial cell lining that was surrounded by few GFP-macrophages in the interstitium without evidence of fibrosis (FIG. 5D).

Conclusions

CSF-1 administration to mice with IR injury resulted in the promotion of renal repair by accelerated tubular epithelial cell replacement and attenuation of interstitial fibrosis. IR is a model of acute tubular necrosis that is characterized pathologically by tubule cell damage resulting from prolonged renal ischemia. The accumulation of macrophages was distinctly observed in the tubulointerstitium of IR kidneys at 1 week after the initiation of injury. This was associated with numerous tubular casts formed as a result of the complete loss of the loss of functioning tubular epithelial cells leading to diffuse effacement and loss of the proximal tubule cell brush border. In IR kidneys large numbers of macrophages were also evident in the interstitium due to inflammation induced from hypoxic insult. Elevated urine protein levels were also observed in IR mice subsequent to the loss of renal function.

CSF-1 was found to promote both a structural and functional recovery of the kidneys from IR mice. Importantly, CSF-1 treatment was initiated at 3 days after IR injury, a time when renal damage and inflammation is already evident. CSF-1 treatment of IR mice resulted in a restoration of the tubular epithelium, attenuation of interstitial matrix expansion and recovery of renal function, comparable to control kidneys.

Markedly reduced numbers of interstitial macrophages were observed in the in CSF-1-treated IR kidneys, compared to IR kidneys without treatment. The population of macrophages observed in the IR mice with CSF-1-treatment appeared to surround re-epithelialised renal tubules and were present without evidence of extracellular matrix accumulation.

Example 4

Materials and Methods

Newborn Mouse Analysis

C57/B 16 mice were time-mated and the mouse pups given three intraperitoneal (i.p.) injections of recombinant human CSF-1 (Chiron Corporation, Emeryville, Calif., USA) at days 1, 2 and 3 after birth. The CSF-1 was administered at a dose of 1 µg/g body weight at a concentration of 1 µg/ml where the final volume did not exceed 50 µl per injection. Litter mate aged-matched control mice received vehicle (phosphate buffered saline) control injections of the same volume. The CSF-1-treated mouse pups were toe and tail clipped for identification and returned to their mothers. The CSF-1-treated mouse pups and the control-treated pups were killed at day 29 for light microscopy of kidney and lung histology and estimation of glomerular number. Histology Kidney and lung tissue was taken from CSF-1-treated and litter mate control-treated mice, immersion fixed in 4% paraformaldehyde and processed on short cycle before embedding into paraffin for histological analysis.

The paraffin-embedded kidneys were each sectioned at 4 microns using a microtome (Leitz Wetzlar, Germany), and the sections were then placed on poly-L-lysine slides and left to adhere for 3 hours at 70° C. The slides were dewaxed in xylene, rehydrated through graded alcohols to water before staining with haematoxylin and eosin by standard methods.

Stereological Assessment of Glomerular Number and Kidney Volume

At day 29, mice with/without delivery of CSF-1 were killed and their kidneys removed and processed for methacrylate embedding and subsequent stereological counting. The processing involved placing the kidneys into 10% formalin for 48 hours, 70% ethanol overnight, and then three one hour washes with 100% ethanol followed by butanol overnight and 72 hours in infiltration solution (Technovik 7100, Electron Microscopy Sciences, QLD). Kidneys were then embedded in methacrylate resin (Technovik 7100) and left to set for three days. Once set, the backs of blocks were made using Technovik 3040 solution (Technovik, Electron Microscopy Sciences, QLD) and allowed to set for one hour. Sections were then serial sectioned at 20 µm using a microtome, and every 10th and 11th section was collected beginning at a random number.

Sections were stained using periodic acid-Schiff (PAS) staining, however the time in reagents was extended compared to a standard paraffin protocol, due to the slow rate of penetration through the resin.

Stereological counting was performed firstly on a micro fische reader to determine kidney volume using the Cavalieri Principal (Kett, M M et al., 1996). Complete sections were used for nephron number estimation using a physical dissector/fractionator combination (Bertram, J F, 1995)—whereby pairs of sections are projected onto an unbiased 2×2 cm counting grid. Grid points that lay upon kidney tissue, glomeruli and renal corpuscles were tabulated, as were glomeruli disappearing events across each slide. Using a formula, the nephron number was estimated.

Results and Discussion

Figure 6:
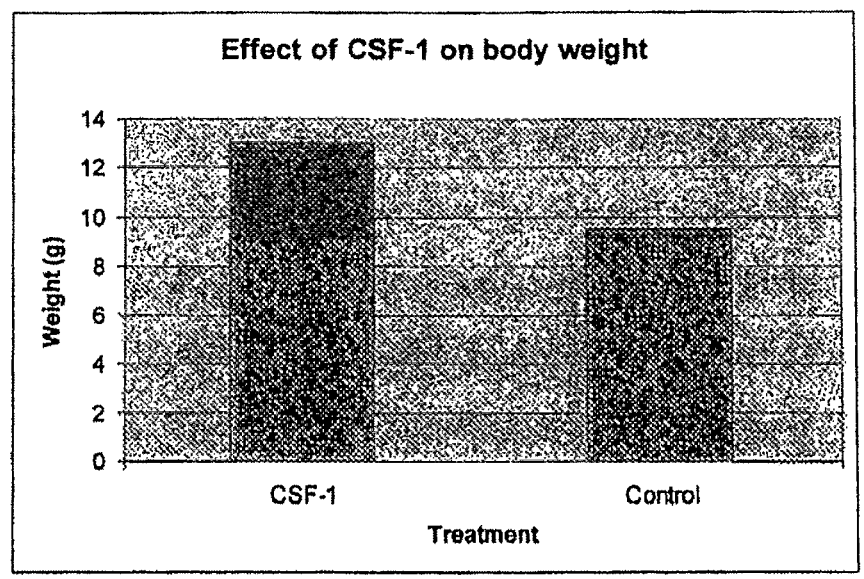
FIG. 6 provides a graph demonstrating the average mouse body weight (n=3/group) in mice receiving CSF-1 compared to litter mate control treated mice.
Figure 7:
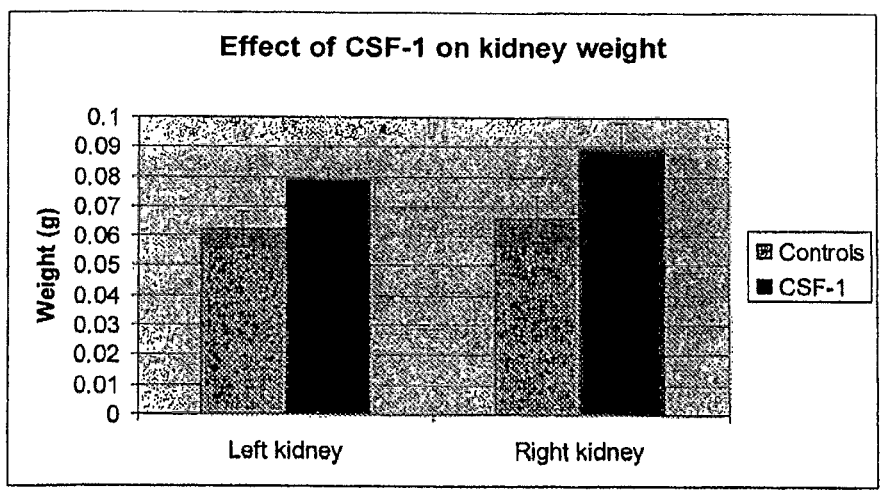
FIG. 7 provides a graph showing the effect on kidney weight of CSF-1 delivery to newborn mouse pups.
Figure 8:
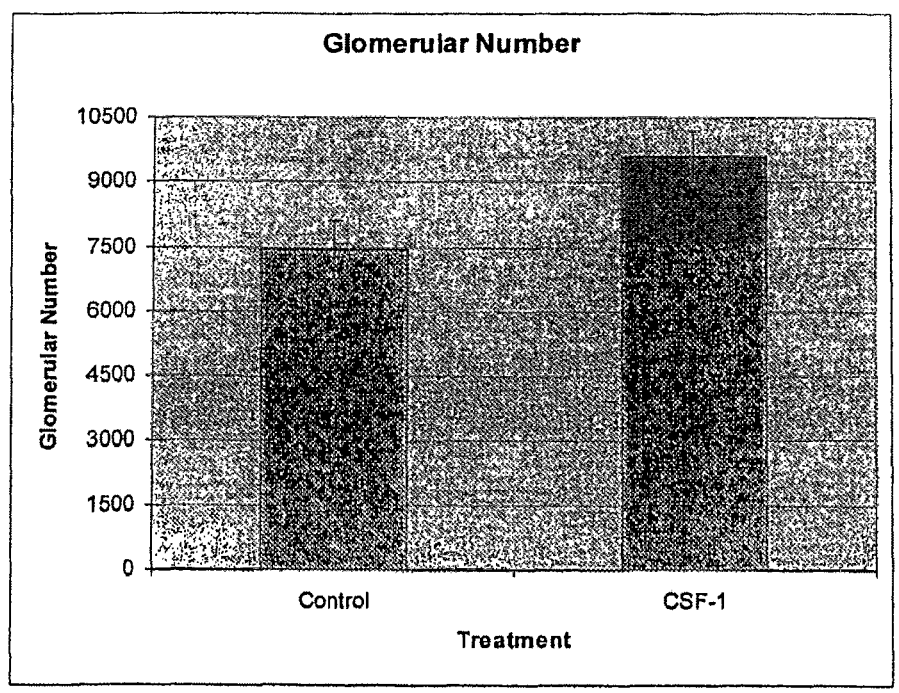
FIG. 8 provides a graph showing a stereological estimation of glomerular number in the kidneys from mice receiving CSF-1 or phosphate buffered saline (PBS).

The administration of CSF-1 (1 µg/g body weight) was given to mouse pups at Day 1, 2 and 3 after birth. In CSF-1-treated mice, there was an overall increase in body weight (FIG. 6) and individual kidney weights (FIG. 7). Mice killed at day 29 we observed to have a 37% increase in overall body weight compared to age-matched litter mates. CSF-1-treated mice had a 27% and 33% increase in left and right kidney weights, respectively, at the same timepoint. The mice with CSF-1 treatment were also found to have a 29% increase in the number of kidney glomeruli compared to age-matched litter mate control mice treated with phosphate buffered saline (FIG. 8). This demonstrates that CSF-1 can promote increased nephro genesis that is associated with increased kidney growth.

Figure 9:
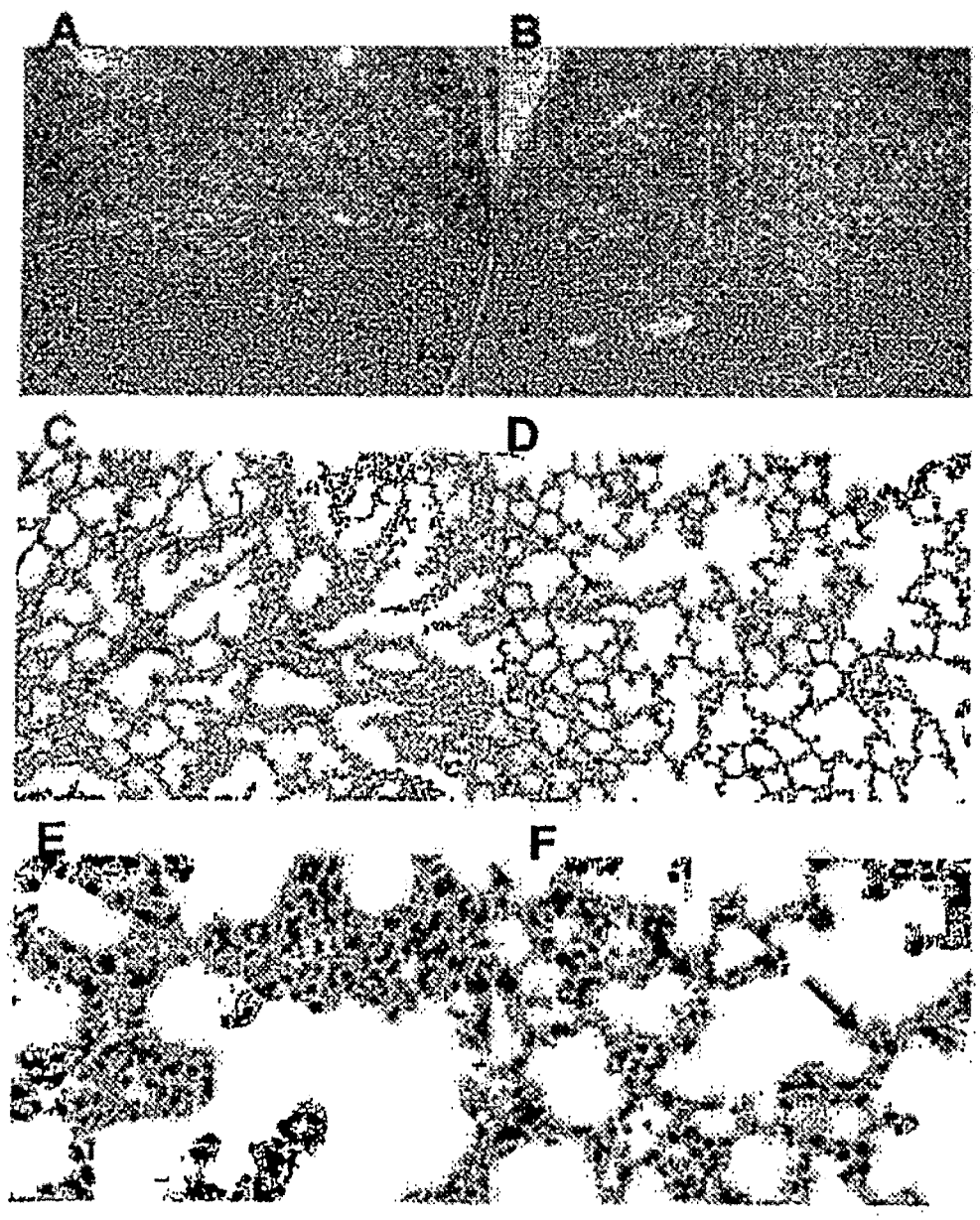
FIG. 9 shows the histology of kidneys from control (A; Mag ×100) and CSF-1 treated mice (B; Mag ×100) killed at day 29 and stained with haematoxylin and eosin; and the histology of lungs of control (C; Mag ×200, E; Mag ×400) and CSF-1-treated (D; Mag ×200, F; Mag ×400) mice.

FIG. 9 demonstrates the histology of the kidneys and lungs from CSF-1 (FIG. 9B, D, F) and control-treated (FIG. 9A, C, E) mice at day 29. There were no obvious structural abnormalities observed in the kidneys from mice following CSF-1 injection compared to control animals. On the other hand, the lungs from CSF-1-treated mice appeared more developed; in particular, the alveolar wall appeared to be thinner and less cellular, and there was less connective tissue compared to litter mate control animals. This corresponds to a greater degree of alveolarisation in the CSF-1-treated animals.

In conclusion, CSF-1 was observed to have a growth promoting effect on total and individual kidney weights when administered systemically to newborn mice. This increase in kidney weight in the CSF-1 treated mice was associated with increased, nephrogenesis. In addition, the lungs of the CSF-1 treated mice appeared more differentiated compared to control litter mate animals. Therefore, it is considered that CSF-1 shows considerable promise for the treatment of pregnant mothers at risk of premature delivery, as well as in the treatment of premature babies with the objective to promote growth and maturation of the lungs and kidneys to prevent associated complications and disorders.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention described herein has been supported by a research grant from the National Institutes of Health (USA).

Throughout this specification, the aim has been to describe the preferred embodiments of the invention without limiting the invention to any one embodiment or specific collection of features. Various changes and modifications may be made to the embodiments described and illustrated herein without departing from the broad spirit and scope of the invention.

All computer programs, algorithms, patent and scientific literature referred to in this specification are incorporated herein by reference in their entirety.

All publications mentioned in this specification are herein incorporated by reference. Any discussion of documents, acts, materials, devices, articles or the like which has been included in the present specification is solely for the purpose of providing a context to the disclosed embodiments. It is not to be taken as an admission that any or all of these matters form part of the prior art base or were common general knowledge in the field relevant to the present inventions as it existed in Australia or elsewhere before the priority date of each claim of this application.

It will be appreciated by persons skilled in the art that numerous variations and/or modifications may be made to the disclosed embodiments as shown herein without departing from the spirit or scope of the inventions as disclosed. The present embodiments are, therefore, to be considered in all respects as illustrative and not restrictive.

What is claimed is:

1. A method of treating reduced renal function in an infant or fetus in need thereof, comprising:
   administering to the infant or fetus a therapeutically effective amount of a pharmaceutical composition comprising:
   i) colony stimulating factor-1 protein (CSF-1);
   ii) a biologically active fragment of CSF-1; or
   iii) a biologically active CSF-1 analog comprising a region having at least 85% homology with a region of CSF-1 responsible for biological activity of CSF-1;
   wherein the treated infant or fetus has an improvement in renal function, comprising a promotion in kidney development, an increase in kidney weight or volume, an increase in kidney growth, an increase in nephrogenesis, an increase in the number of nephrons, enhanced nephrogenesis, or kidney maturation.

2. The method of claim 1, wherein the administered pharmaceutical composition comprises the CSF-1.

3. The method of claim 1, wherein the administered pharmaceutical composition comprises the biologically active fragment of CSF-1.

4. The method of claim 1, wherein the administered pharmaceutical composition comprises the biologically active CSF-1 analog.

5. The method of claim 4, wherein the biologically active CSF-1 analog comprises a region having at least 90% homology with a region of CSF-1 responsible for biological activity of CSF-1.

6. The method of claim 4, wherein the biologically active CSF-1 analog comprises a region having at least 95% homology with a region of CSF-1 responsible for biological activity of CSF-1.

7. The method of claim 1, wherein the reduced renal function resulted from low birth weight or from premature birth of the infant or fetus.

8. The method of claim 1, wherein the infant or fetus has low birth weight.

9. The method of claim 1, wherein the infant or fetus has a reduced number of nephrons or an underdeveloped kidney.

10. The method of claim 9, wherein the underdeveloped kidney resulted from low birth weight or from premature birth of the infant or fetus.

11. The method of claim 1, wherein the pharmaceutical composition is a nebulizable or injectable composition.

12. The method of claim 1, wherein the pharmaceutical composition is administered by intravenous infusion, nebulization treatment, or aerosol delivery.

13. The method of claim 1, wherein the pharmaceutical composition is administered systemically or locally.

14. The method of claim 1, wherein the pharmaceutical composition further comprises one or more of a pharmaceutically acceptable excipient, surfactant, vehicle, or diluents.

15. The method of claim 1, wherein the amount administered is at a concentration of up to 500 ug/kg/day.

16. The method of claim 1, wherein the pharmaceutical composition is administered continuously over 8 hours, for 1-7 consecutive days.

17. The method of claim 1, wherein the pharmaceutical composition is administered at a rate such that up to 100 mg of the CSF-1, the biologically active fragment of CSF-1, or the biologically active CSF-1 analog, is delivered to the infant or fetus in need thereof, per hour.

18. A method of treating an infant or fetus having an underdeveloped kidney, comprising:
   administering to the infant or fetus a therapeutically effective amount of a pharmaceutical composition comprising:
   i) colony stimulating factor-1 protein (CSF-1);
   ii) a biologically active fragment of CSF-1; or
   iii) a biologically active CSF-1 analog comprising a region having at least 85% homology with a region of CSF-1 responsible for biological activity of CSF-1;
wherein the treated infant or fetus has a promotion in kidney development, comprising an increase in renal function, an increase in kidney weight or volume, an increase in kidney growth, an increase in nephrogenesis, an increase in the number of nephrons, enhanced nephrogenesis, or kidney maturation.

19. The method of claim 18, wherein the wherein the administered pharmaceutical composition comprises the CSF-1.

20. The method of claim 18, wherein the administered pharmaceutical composition comprises the biologically active fragment of CSF-1.

21. The method of claim 18, wherein the administered pharmaceutical composition comprises the biologically active CSF-1 analog.

22. The method of claim 21, wherein the biologically active CSF-1 analog comprises a region having at least 90% homology with a region of CSF-1 responsible for biological activity of CSF-1.

23. The method of claim 21, wherein the biologically active CSF-1 analog comprises a region having at least 95% homology with a region of CSF-1 responsible for biological activity of CSF-1.

24. The method of claim 18, wherein the infant or fetus has low birth weight.

25. The method of claim 18, wherein the underdeveloped kidney has a reduced number of nephrons or reduced kidney weight.

* * * * *